US005597718A

United States Patent [19]
John et al.

[11] Patent Number: 5,597,718
[45] Date of Patent: Jan. 28, 1997

[54] GENETICALLY ENGINEERING COTTON PLANTS FOR ALTERED FIBER

[75] Inventors: Maliyakal E. John, Middleton; Paul F. Umbeck; Winston J. Brill, both of Madison, all of Wis.

[73] Assignee: Agracetus, Middleton, Wis.

[21] Appl. No.: 530,797

[22] Filed: Sep. 20, 1995

Related U.S. Application Data

[63] Continuation-in-part of Ser. No. 138,814, Oct. 18, 1993, abandoned, which is a continuation of Ser. No. 617,239, Nov. 21, 1990, abandoned, which is a continuation-in-part of Ser. No. 253,243, Oct. 4, 1988, abandoned.

[51] Int. Cl.$^6$ .............................. C12N 15/29; C12N 5/14; C12N 15/82; A01H 5/00
[52] U.S. Cl. .................... 435/172.3; 435/69.1; 536/23.6; 536/24.5; 800/205; 800/DIG. 63; 935/4; 935/64
[58] Field of Search ............................ 435/172.3, 69.1, 435/240.4, 240.5; 800/205, DIG. 63; 536/23.6, 24.5; 935/4, 64

[56] References Cited

U.S. PATENT DOCUMENTS 4,771,002  9/1988  Gelvin ................................. 435/172.3

FOREIGN PATENT DOCUMENTS

| 0270355 | 6/1988 | European Pat. Off. . |
| 0218571 | 4/1992 | European Pat. Off. . |
| WO8504899 | 11/1985 | WIPO . |

OTHER PUBLICATIONS

Anderson, M. A., et al., "Cloning of cDNA for Stylar Glycoprotein Associated with Expression of Self–Incompatibility in *Nicotiana alata*," *Nature* 321:38–44 (May 1, 1986).
Ausubel, F., et al., *Current Protocols in Mol. Biol.*, Wiley (1987).
Besley, C. A., and I. P. Ting, "The Effects of Plant Growth Substances on In Vitro Fiber Development from Fertilized Cotton Ovules," *Amer. J. Bot.* 60:130–139 (1973).
Firoozabady, E., et al., "Transformation of Cotton (*Gossypium hirsutum* L.) by *Agrobacterium tumefaciens* and Regeneration of Transgenic Plants," *Plant Mol. Biol.*, 10:105–116 (1987).
Gebhart, F., "Calgene Expresses Recombinant Genes for Herbicide Tolerance," *Genetic Engineering News* (1985).

John, M. E., et al., "Identification and Characterization of cDNA Clones Specific for Cholesterol Side–Chain Cleavage Cytochrome p–450," *Proc. Natl. Acad. Sci. U.S.A.*,, 81:5628–5632 (1984).
Klausner, A., "Researchers Cotton to New Fiber Findings," *Bio/Tech.*, 3:1049–1051 (1985).
McCormick, S., et al., "Leaf Disc Transformation of Cultivated Tomato (*L. esculentum*) Using *Agrobacterium tumefaciens*," *Plant Cell Reports*, 5:81–84 (1986).
Meinert, M. C., and D. P. Delmer, "Changes in Biochemical Composition of the Cell Wall of the Cotton Fiber During Development," *Plant Physiol.*, 59: 1088–1097 (1977).
Peterson, M. W., et al., "Study of Fiber Synthesis Related Genes in Fiber Producing and Non–Fiber Producing Species of the Genus Gossypium," *Agronomy Abstract* (Oct. 1988).
Rangan, T. S., et al., "Somatic Embryogenesis in Tissue Cultures of *Gossypium hirsutum* L.", In Vitro 20:256 (1984).
Trulson, A. J., et al., "Transformation of Cucumber (*Cucumis sativus* L.) Plants with *Agrobacterium rhizogenes*," *Theor. Appl. Genet.*, 73: 11–15 (1986).
Zhou, G–Y, et al., "Introduction of Exogenous DNA into Cotton Embryos," *Methods in Enzymology*, 101:433–481 (1983).
Wilke–Douglas 1986 Physiol. Plantarum 68:560–565.
Beasley, C. A. and I. P. Ting, "The Effects of Plant Growth Substances on In–Vitro Fiber Development from Fertilized Cotton Ovules," *Amer. J. Bot.* 60:2:130–139 (1973).
Umbeck, P. et al., "Genetically Transformed Cotton (*Gossypium hirsutum* L.) Plants," Bio/Technology 5:3:263–266 (Mar. 1987).
Shoemaker, et al., "Characterization of Somatic Embryogenesis and Plant Regeneration in Cotton (*Gossypium hirsutum* L.)", Plant Cell Reports 5:3:178–181 (1986).
Velten, J. and J. Schell, "Selection Expression Plasmid Vectors for Use in Genetic Transformation of Higher Plants," Nucleic Acids Research 13:19:6981–6998 (1985).

*Primary Examiner*—Patricia R. Moody
*Attorney, Agent, or Firm*—Quarles & Brady

[57] ABSTRACT

A method is disclosed which describes the identification of cDNA clones useful for identifying fiber genes in cotton. The cDNA clones are useful in developing corresponding genomic clones from fiber producing plants to enable genetic engineering of cotton and other plants using these genes. The fiber-specific genes are identified by differential cDNA library screenings. Coding sequences from these isolated genes are used in sense or antisense orientation to alter the fiber characteristics of transgenic fiber-producing plants.

2 Claims, 4 Drawing Sheets

GENETICALLY ENGINEERING COTTON PLANTS FOR ALTERED FIBER

CROSS REFERENCE TO RELATED APPLICATION

This is a continuation-in-part of application Ser. No. 08/138,814 filed Oct. 18, 1993 now abandoned, which is a continuation of Ser. No. 07/617/,239 filed Nov. 21, 1990, now abandoned, which is a CIP of Ser. No. 07/253,243, filed Oct. 4, 1988, now abandoned.

FIELD OF THE INVENTION

The present invention relates to the general technology of plant genetic engineering and, in particular, to the identification of genes that are expressed only in fiber or genes the expression of which influences fiber development, fiber characteristics, and cellulose synthesis in cotton, and the use of those genes to create novel genetically transformed cotton (Gossypium) plants and lines with varied cotton fiber characteristics and quality.

BACKGROUND OF THE INVENTION

The hurdle of creating successful genetically engineered plants in major crop varieties is now being overcome sequentially on a plant by plant basis. While plant genetic engineering has been successfully demonstrated in several model plant species, most notably tobacco, carrot and petunia, these species are not considered to be economically important plant species for agricultural purposes. Researchers have therefore directed their efforts toward the genetic engineering of commercially important crop plants so that they may be improved through the use of genetic engineering.

The term "genetic engineering," as used herein, is meant to describe the manipulation of the genome of a plant, typically by the introduction of a foreign gene into the plant, or the modification of the genes of the plant, to increase or decrease the synthesis of gene products in the plant. Typically, genes are introduced into one or more plant cells which can be cultured into whole, sexually competent, viable plants which may be totally transformed or which may be chimeric, that is having some tissues transformed and some not. These plants can be self-pollinated or cross-pollinated with other plants of the same or compatible species so that the foreign gene or genes, carried in the germ line, can be inserted into or bred into agriculturally useful plant varieties.

Current strategies directed toward the genetic engineering of plant lines typically involve two complementary processes. The first process involves the genetic transformation of one or more plant cells of a specifically characterized type. The term "transformation" as used herein, means that a foreign gene, typically a chimeric gene construct, is introduced into the genome of the individual plant cells, typically through the aid of a vector, which is integrated into the genome of the plant. The second process then involves the regeneration of the transformed plant cells into whole sexually competent plants. Neither the transformation nor regeneration process need be 100% successful, but must have a reasonable degree of reliability and reproducibility so that a reasonable percentage of the cells can be transformed and regenerated into whole plants.

Although successful transformation and regeneration techniques have been demonstrated in model plant species Barton et al., *Cell* 32:1033 (1983), wherein the transformation and regeneration of tobacco plants was reported, similar results with cotton have only been achieved relatively recently. Umbeck et al. *Bio/Technology*, 5:3, pp. 263≧266 (1987); Firoozabady et al., *Plant Mol. Bio.*, 10, pp. 105–116 (1987).

Successful transformation and regeneration of genetically engineered cotton plants has the potential to be of significant value to this agriculturally important crop. One of the most important benefits potentially achievable from genetically engineering cotton plants is the alteration and modification of cotton fiber quantity and quality. Cotton fibers develop from epidermal cell layers of the ovule in the cotton plant. The single epidermal cells elongate to become fiber cells which synthesize an abundance of cellulose which is deposited in the form of a secondary wall structure in the cell. In the cotton fiber cell, cellulose is produced in a pathway leading from UDP-glucose by a number of enzymes including cellulose synthase. The quality of the cotton fiber is dependent on such factors as the extent of elongation and degree of secondary wall deposition. It is assumed that a number of genes as well as environmental factors regulate the physical characteristics of the fiber, such as length, thickness and micronaire value. However, the genes responsible for cellulose synthesis and fiber development in cotton plants are heretofore entirely uncharacterized at a molecular level.

The domesticated plants known as cotton are actually of several species. For example, the cultivars of Coker 312, PD3, Naked Seed are varieties of *Gossypium hirsutum*, while the cultivars Pima (S6) and Sea Island (Barbados) are varieties of *G. barbadense*. Different species of cotton are grown in different geographical locations and have different fiber qualities. Previously, the transfer of traits from species to species has proven difficult because of the incompatibility of the germplasms of the different species and the resultant hybrid instability. It is a goal of researchers in the cotton field to be able to obtain desired fiber characteristics in cultivars of high yield. For example, a cotton cultivar adapted to a specific geographic region may yield long, fine fibers with poor or moderate yield, while a second cotton cultivar at a different location may have excellent yield of fibers with shorter coarse fibers. It would be advantageous to be able to combine the characteristics of each of the fibers of the plants by genetically transforming one plant with the genes directed to the fiber characteristics of a second, different plant.

SUMMARY OF THE INVENTION

It is therefore an object of the present invention to genetically engineer whole intact cotton plants and lines in order to alter fiber quantity and quality.

It is further an object of the present invention to identify genes which contribute to or regulate fiber production in cotton or other fiber producing plants.

It is still further an object of the present invention to introduce genes from cotton plant having fiber of one type into plants of a different cotton plant having a second fiber type.

It is yet another object of the present invention to modify the coding sequences, non-coding sequences or regulatory sequences of the fiber production genes to modify the production of fiber producing plants.

These objects and others are fulfilled by the present invention which involves a method of changing the fiber quality of fiber-producing plants, such as cotton. The method first involves identifying genes that contribute to fiber quality in fiber-producing cells of a first plant. This may be performed by isolating the intact functional mRNA from fiber producing cells, making a complementary DNA (cDNA) library of cDNA clones from the mRNA, and screening the library with cDNA generated from other tissues to eliminate genes that are expressed in tissues other than those which produce fiber. This screening procedure will result in the identification of cDNA clones that are expressed preferentially in fiber cells. Although the plant may be any of a number of varieties of fiber producing plants, cotton (Gossypium) plants are the preferred plants for purpose of the present invention. After the identification process is complete, cDNA clones are used to create plant expression vectors that may be introduced into a second fiber-producing plant. The transformation process may be conducted by Agrobacterium-mediated transformation, particle-mediated transformation or other methods known to the art.

The present invention is a useful genetic engineering tool for the identification and introduction of altered fiber-specific characteristics into cotton plants. The identification and introduction of fiber genes from one variety to another can be extended to include other exotic plants that produce fiber. Many of these plants will have fibers with one or more desirable qualities, which can be incorporated into a cotton plant.

DETAILED DESCRIPTION OF THE INVENTION

Figure 1:
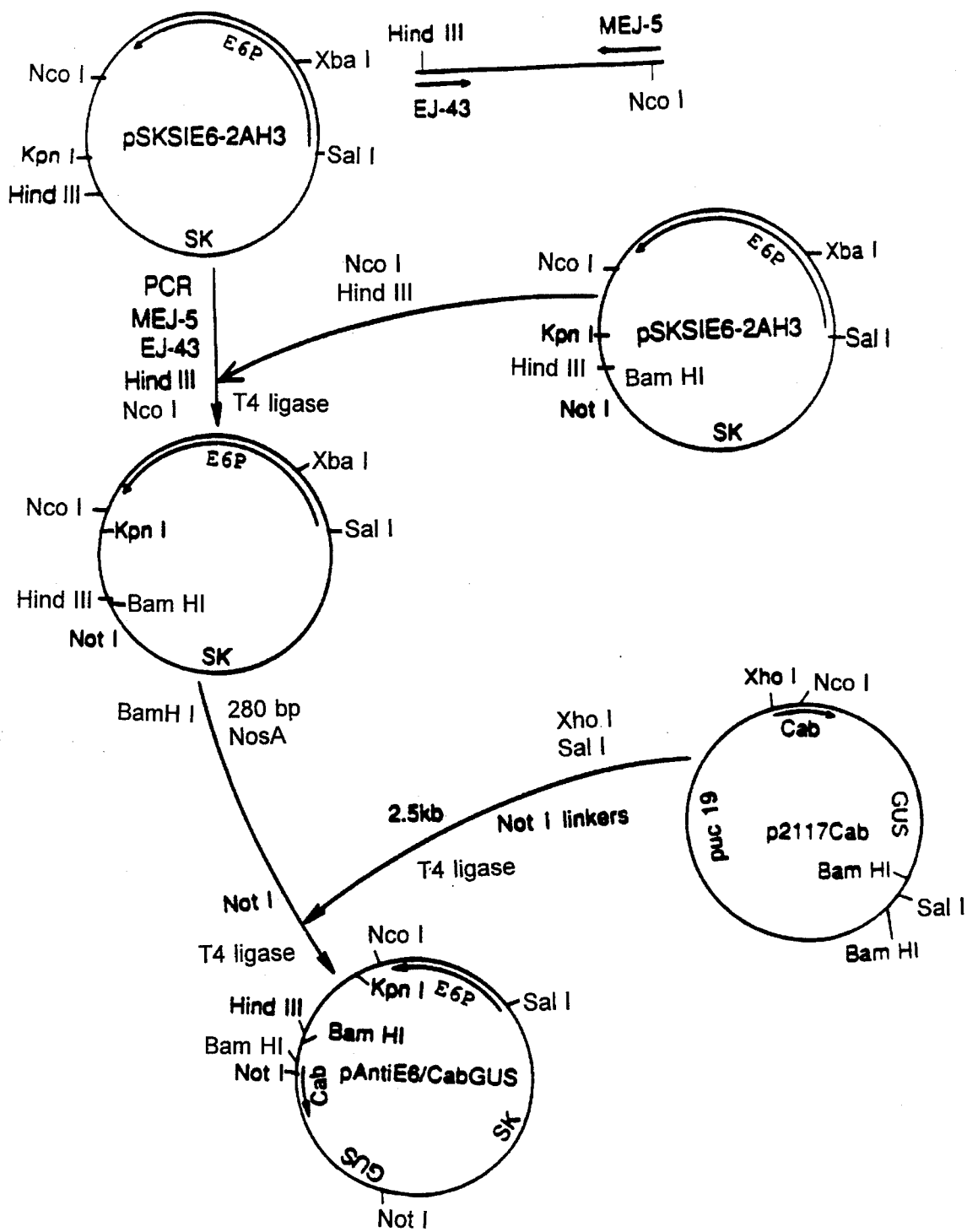
FIG. 1 is a diagram of the construction of a plasmid containing an antisense version of the E6 message.

The present invention is generally directed to the modification or alteration of fiber quality in cotton plants, and may involve three related processes:

(1) the identification of gene products (i.e. mRNAs) in a first fiber producing plant which are specific to fiber cells and the use of those gene products (i.e. mRNAs) to identify the genes which code for those products, i.e., the fiber genes;

(2) transformation of a second fiber producing plant, normally not possessing copies of that particular gene, with genetic constructions including the identified fiber genes from the first plant; and (3) the modification of the expression of a fiber gene in a plant, by altering its regulatory sequences or by using antisense genetic constructs to inhibit or alter the expression of a native fiber gene.

The invention envisions the genetic transformation of one variety of cotton plant by the introduction of DNA constructions including a fiber gene from a second, different variety of cotton plant or by the alteration of a native fiber gene. Non-limiting examples which may be used for the present invention as either the source of the fiber genes or the plant which is transformed include plants belonging to (*Gossypium arboreum, G. herbaceum, G. barbadense*), and (*G. hirsutum*). Additionally, the process of the present invention may incorporate fiber genes from other exotic plants which produce cellulose fiber. Many of these plants will have fibers with one or more desirable qualities, which can then be incorporated into the cotton plant. Such plants include the Silk Cotton Tree (Kapok, *Ceiba pentandra*), Desert Willow, Creosote Bush, Winterfat, Balsa, Ramie, Kenaf, Hemp, Roselle, Jute, Sisal Abaca and Flax.

The identification of fiber genes can begin with gene products most conveniently identified at the RNA level. In order to identify the gene products that are specific for fiber, the mRNA from fiber producing cells are compared with mRNA profiles of a number of different tissue types from the same plant, and the mRNAs which are specific to fiber cells, are identified. This is accomplished by preparing cDNA libraries from isolated RNAs from the various developmental stages of fiber producing cells, and using differential hybridizations to eliminate all clones that hybridize to RNAs produced in other tissues of the same plants. The results of this procedure will include both cDNA clones for RNA's that are produced only in fiber cells in the cotton plant and cDNA clones for RNA's that are produced differentially in cotton plants such that they are produced at much higher levels in fiber producing cells than in other cells of the plant. These cDNA clones can be used to identify genomic clones from a genomic library from the same fiber producing plant or from other plants with corresponding genes. Alternatively, after appropriate processing, the cDNA clones can be used as coding regions in chimeric expression constructions for use in plant transformations themselves. The same cDNA clones can also be used to construct anti-sense genetic constructs to alter the expression of the corresponding gene in the cells of cotton plants.

Thus the process described here begins with the identification of the genes that contribute to fiber development, so that those fiber genes may be introduced into other species of plants. As used herein, "fiber gene" is used to describe those genes which (1) are expressed only or at least preferentially in fiber producing cells and (2) code for products which influence fiber development or fiber characteristics. The hypothesis of this approach is that if a gene is expressed only in a certain cell type, or very preferentially in that cell type, then it is very likely that the gene product influences the development or takes part in the structural traits unique to that cell type. Genes that show differential expression play a role in the development of fiber. For example, the enzymes responsible for cellulose synthesis may not be unique to fiber cells, since cellulose is a part of all plant cells. Yet at certain developmental stages of the fiber cells, when relatively large quantities of cellulose are synthesized, cellulose synthesis related genes should be more active than in other cell types. Thus the identification of fiber genes by analyzing fiber cell expression enables the commencement of a program of the genetic engineering of cotton to modify or improve fiber quality or quantity.

The identification of fiber genes preferably begins with the identification of fiber specific mRNA's. The sequences of several cDNA clones from such fiber specific mRNA are given below. These cDNA clones were all created by analysis of cotton fiber mRNAs. Conventional method of isolating RNA's from plant cells do not work well with cotton fiber cells. The isolation of high purity DNA or RNA from cotton cells has been notoriously difficult, partly due to the phenolic terperiods and tannins present in cotton cells. Katterman et al., *Preparative Biochemistry*, 13, pp. 347–359 (1983) It has been found that certain modifications of RNA isolation techniques permit the isolation of RNA from cotton fiber cells. The protocol used was based on that set forth in Chirqwin et al., *Biochemistry*, 18, pp. 5294–5299 (1979), modified to include higher buffering capacity, alkaline pH, and the addition of polyvinyl pyrrolidone (PVP). The PVP, in particular, is believed to form hydrogen bonding to phenolics, and are then removed in subsequent steps. While others have suggested the use of PVP for other plant systems, the significance of the addition of this additive to the successful isolation of total mRNA from cotton fiber cells has not previously been demonstrated. Lichtenstein and Draper in *Genetic Engineering of Plants, DNA Cloning*, Vol II, Glover, Ed., pp. 101–110 (1985).

Stable integration of expressing foreign genes into cotton plants has been demonstrated and repeated. Umbeck et al., *Bio/Technology*, 5:3 pp. 263–266 (1987); Firoozabady et al., *Plant Mol. Biol.*, 10:pp. 105–116 (1987). Using the techniques taught in each of these papers, the transformation of cotton tissues is accomplished by Agrobacterium infection and regeneration. Although a lengthy process, the Agrobacterium-mediated transformation of cotton has also been practiced by other laboratories and can now readily be replicated by those of ordinary skill in plant genetic engineering. It is to be understood, however, that other methods for the transformation of cotton plants and lines are being studied, and that the transgenic cotton plants and lines with fiber genes introduced into them will prove advantageous and useful regardless of the method of transformation of the original tissues. Specifically, it has now been demonstrated that higher plants can be stably genetically transformed by particle mediated transformation techniques, which avoid many of the difficulties and delays inherent in plant regeneration required by Agrobacterium plant transformation. McCabe et al., *Bio/Technology*, 6:8, 923–926 (1988). Recent research results suggest that routine particle mediated transformation of cotton is to be expected shortly.

In the introduction of fiber genes into cotton plants, there are several approaches possible for expression of the genes, or alteration of fiber genes, in the transgenic cotton plants. One method is to use complete mRNAs to generate cDNAs of the protein coding sequence. The cDNA sequence can then be combined with a plant expression cassette demonstrated to express an inserted coding sequence in cotton plants, and the chimeric expression cassette can then be introduced into cotton plants. This approach should lead to constitutive or regulated expression of the genes in the transgenic plant depending on the characteristics of the particular promoter used in the expression cassette. In most instances it is desirable for the fiber specific genes to be developmentally regulated so as to be expressed only in fiber cells at a proper developmental stage. This can be most expeditiously accomplished by using the cDNA clones from fiber specific mRNAs to find genomic clones from a genomic library of the plant. From the genomic clone, the entire fiber-specific gene, including developmentally regulated promoter and regulatory sequences, can be isolated. This entire intact fiber-specific gene can then be inserted into other cotton lines, in which case the gene should be normally regulated so as to express only in fiber tissues.

Another approach to creating cotton plants with altered fiber characteristics is to create antisense genetic constructs to inhibit or lessen the expression of one or more fiber genes in fiber cells. The theory behind antisense genetic constructs is that the production of RNA strands in the cells of an organism which are complementary to the mRNA of an endogenous gene will result in hybridization of the antisense RNA to the native mRNA resulting in decreased expression of the mRNA gene. Thus in an antisense construct, a complete coding sequence for the mRNA is not needed. All that is needed is a sequence of sufficient length to construct a selectively hybridizing antisense RNA. Thus the cDNA clones discussed below are of particular utility for this approach.

The following is a description of the process and materials used to identify fiber genes and transformation of cotton plants. Although reference to cotton is specifically made, it is within the scope of the present invention to substitute other fiber-producing plants.

EXAMPLES

IDENTIFICATION OF FIBER GENES

1) Isolation of RNA From Fiber

Fiber cells, at different stages of development, from fiber-producing plants were collected and quick-frozen in liquid nitrogen. Specifically, fiber cells from 10, 15 and 23 day old Coker 312 cotton plants were collected and quick-frozen. The frozen fiber cells were then powdered in a mortar in liquid nitrogen and homogenized for 1.5 minutes using a polytron in a homogenization buffer at full speed. The homogenization buffer included the following ingredients: 5M Guanidine isothiocyanate, 0.2M Tris- acetate (pH 8.5), 0.7% Beta mercaptoethanol, 1% polyvinyl pyrrolidone (PVP, MW 4U Kd), and 0.62% sodium Lauryol sarcosine. Beta mercaptoethanol and PVP were added just before use. A ratio of 1:2 of tissue (weight) to buffer (volume) was used.

The homogenate was filtered through Mira cloth and layered over a 1.5 ml pad of 5.7M cesium chloride as described by Chirgwin, J. M. et al. *Biochemistry*, 18:5294–5299 (1979). The homogenate was then centrifuged for 18 hours at 36,000 rpm in a SW 50.1 rotor at 20° C. After centrifugation, the RNA was collected as described by Chirgwin, J. M., et al., (supra). The RNA was then further purified by Phenol:chloroform extractions and precipitations in the presence of ammonium acetate as described for DNA by Crouse, J. and Amorese, D., *Focus*, 9:2, 3–5 (1987). Poly(A)$^+$ RNA was obtained by oligo (dT) chromatography as described by Maniatis, et al., in *Molecular Cloning: A Laboratory Manual*, Cold Spring Harbor Laboratory, Cold Spring Harbor, N.Y., (1982).

2) Library Construction and cDNA Clone Identification

Complementary DNA libraries were prepared from the mRNA according to the protocol developed by D'Alessio, J. M. et al., *Focus*, 9:1,1–4 (1987) with the following exceptions: The first strand of cDNA was synthesized using a primer having the following sequence dATGCTGG-TACC(T)15; the second strand synthesis was carried out as described by D'Alessio et al., supra, for tailing; The dC tails were added to the double stranded cDNA and then annealed to dG tailed pBR322 plasmid vector (Bethesda Research Laboratories); the recombinant plasmids were used to transform *Escherichia coli* (*E. coli*) RR1 strain as described by Hanahan in *DNA Cloning a Practical Approach*, Vol. 1 (1985) p. 109–135. The transformed cells were selected on antibiotic tetracycline (12 mg/liter) containing agar plates.

Separate cDNA libraries were constructed from the mRNAs from 10 day, 15 day, and 23 day old fiber cells. For the 10 day fiber cell mRNAs, an oligo (dT) primer was used instead. The 10 day cells were selected to be representative of genes active during the primary cell wall stage of cell development. In the 15 day old cell, both primary cell wall and secondary cell wall synthesis systems are active. The 23 day old cells were selected to be representative of genes active principally during secondary wall synthesis.

The clones in the library were then transferred to nitrocellulose filters and duplicate filters were made according to Hanahan, D. and M. Meselson, *Gene*, 10: 63–67 (1980). About 25,000 clones from the 15 day and 23 day libraries were screened using the following procedure. 32-P labelled single stranded cDNAs probes were prepared from poly(A)$^+$ RNAs using 32-P dCTP and reverse transcriptase as described by Maniatis et al., supra. Probes were prepared from poly(A)$^+$ RNAs of 15-day, 23-day old fiber producing cells, and from 0-day ovule, leaf, root and flower cells. Prewashings, prehybridizations, hybridizations and washings of the filters were performed as described in detail in John et al., *Proc. Natl. Acad. Sci. USA*, 81:5628–5632 (1984).

The autographic signals from filters hybridized with 32-P cDNAs from the different tissues were then compared and the clones which hybridized to cDNAs from fiber producing cells, but not to cDNAs from other tissues, were selected. The resulting clones were then subjected to a second cycle of differential screening as described above and additional clones were eliminated as non-fiber specific. This process was continued for a third and then a fourth time. This repetitive screening was to eliminate clones which showed hybridization to other than cDNAs from fiber producing cells. The final collection of clones were then subjected to Northern analysis. For this analysis, poly(A)$^+$ RNA from different tissues were denatured in the presence of formaldehyde and size fractionated on 1.5% agar/formaldehyde gels as described by John et al., s. The RNAs were then blotted to nitrocellulose and probed with 32-P labelled inserts of each individual clone. The clones that showed hybridization to only RNAs from fiber producing cells were selected as fiber genes. This screen resulted in the identification of cDNAs specific to five fiber specific genes. All manipulations on plasmid DNAs such as isolation, purification on cesium chloride gradients, restriction digestion, insert purifications by gel electrophoresis and electroelutions and 32-P labelling by nick translations have been described previously (Maniatis et al., supra and John et al., s).

The cDNA library from the 10-day old cells were then screened using a subtractive hybridization procedure as described below. Following this procedure, the 32-P labelled cDNA from fiber was hybridized to excess biotinylate mRNA isolated from leaf tissue. The hybridized cDNA-biotinylated mRNA hybrids as well as the excess biotinylated mRNAs were separated from unhybridized cDNA by extraction with avidin in phenol:chloroform. The streptavidin was partitioned into the organic phase along with any biotinylated nucleic acid while the single stranded cDNA remained in the aqueous phase. This procedure has been described elsewhere, Duguid et al., *Proc. Natl. Acad. Sci. USA*, 85 pp. 5738–5742 (1988).

Substractive hybridization screening of 4788 clones of the 10 day cell library with leaf cell cDNAs resulted in 800 clones not present in the leaf cells. These clones were then screened by cDNAs generated from ovule, flower and root mRNAs. The results of this screening were 79 putatively fiber specific clones. The duplicate clones which hybridized to each other were detected by the procedure of polymerase chain reaction (PCR)(Saiki et al., *Science*, 239 pp. 487–491 (1988)), Southern blotting and hybridization. The PCR reaction was carried out by first mixing 10 microliters of bacterial culture of the cDNA clone added to 90 microliters of distilled water. Then 20 microliters of that mixture was added to a PCR reaction buffer of 50 mM KCl, 10 mM Tris-HCl pH 8.0, 2.5 mM Mg Cl$_2$, 0.01% gelatin, 200 μM each of dATP, dCTP, dTTP and dGTP, 12.5 picomolar each of sense and antisense primers for pBR322, and 0.5 units of Taq polymerase. The sense and antisense primers were, respectively, (1) GACGAATTCGCTAGAGTAAGTAGT-TCGCCAGT and (2) GACGGATCCCCATACCAAAC-GACGAGCGTGAC. The final reaction volume was 52 microliters. The PCR reactions were carried out in a Perkin-Elmer-Cetus thermocycler.

The amplified DNA from the PCR reactions were separated by agarose gel electrophoresis. The gel was blotted to nitrocellulose by the method of Southern, *J Mol. Biol.* 98 p. 503–517 (1975). One or more bacterial clones from the same group were amplified by the same procedure and the products also separated on agarose gel. The amplified insert DNAs were then excised from the gel and purified by electroelution. The purified DNAs, labelled with 32-P by nick translation, were hybridized with the Southern blot. The cross hybridizing clones were thus identified in this fashion. This procedure resulted in the identification of 19 putative fiber specific clones. The clones were further analyzed by Northern blots. Three of the clones were found to be fiber specific. Another five of the clones were found to be differentially expressed to a higher degree in fiber and to a lesser degree in other tissues.

3) Preparation of Genomic DNA

Genomic DNA from Sea Island cotton and from Kapok were prepared according to the methods of Richards, E. described in *Current Protocols in Molecular Biology*, (Eds. Ausbel, F. M. et al.) Wiley, (1987) pp. 2.3.12.3.3, with the following modification: the frozen plant material was homogenized in extraction buffer containing 1% polyvinyl pyrrolidone. The purified genomic DNA was digested with restriction endonucleases and transferred to nitrocellulose filters by the Southern blotting technique. Southern, E. M., *J. Mol. Biol.*, 98:503–517 (1975).

The filters were then probed with nick translated inserts of the fiber-specific cDNA clones previously identified. The hybridization and blot washing conditions are described in John et al. (supra).

Sea Island cotton and Kapok genomic libraries were prepared by Clonetec, Inc., of California, in EMBL-3 vectors. Inserts of about 10–15 kilobases (kb) were present in these phages. The phage libraries were plated on *E. coli* NM 538 as described in Current Protocols in Molecular Biology, (supra.) Similarly, the library was screened with 32-P labeled inserts of the fiber-specific clones after transferring the library to nitrocellulose filters according to the methods described in *Current Protocols*, (supra) and John et al., (supra).

4) Characterization of fiber specific clones

The following clones have been identified to be fiber-specific based on Northern analysis. The nomenclature for the clones is as follows: CK=Coker, FB=fiber, 10, 15, or 23=age in days of fiber cells, Al and the last character and number stand for clone identity.

a. CKFB15Al-E6

This cDNA clone for a fiber gene has an insert of 983 base pairs. It hybridizes to a broad band of RNA that is indicative of two molecular sizes of 1.0 and 1.1 kb. The RNA is expressed in fiber and not in root or leaf. Both flower and ovule RNAs shows weak hybridization which is probably due to the presence of fiber initials in these tissues (Graves, D. A. and Steward, J. M. *J. Exp. Bot.* 39, pp. 59–69 (1988) The E6 RNA was found to be developmentally regulated. Its steady state concentration increases immediately after anthesis, and shows a decrease at about 16 to 20 days after anthesis. A further increase is noticed at about 24 days and finally it declines at about 30 days. Hybrid selection translation experiments showed that E6 codes for two polypeptides of 26 and 30 kilodalton. The E6 clone also cross hybridizes with Pima and Naked seed cotton fiber cell RNAs. It also cross hybridizes with PD3, Pima, Sea Island, Kenaf, Roselle, and Kapok DNAs. The complete nucleotide sequence of E6 insert has been worked out by Cetus Corp., Emeryville, Calif. The sequence of the E6 insert is presented as SEQ ID No.: 1 and below. This sequence contains a long open reading frame extending from position 1 to position 748. On this same open reading frame, start codons appear at positions 34, 61 and 94. If the first codon is the initiation site for the protein, the 714 nucleotide reading frame would yield a 238 amino acid protein. The derived amino acid composition of the E6 protein is given in Table I. Hybridization experiments indicate that it is coded by one or two genes in the cotton genome.

Sequence of CKFB15A1-E6:

includes 17 pentapeptide repeats of X-Y-Pro-Pro-Pro repeat units where X and Y are serine, alanine and threonine. The H6 protein is clearly distinct from previously known proteins of plant cell walls, such as extensin. Chen and Varner, *EMBO J*, 4, pp. 2145–2151 (1985).

d. CKFB15A1-C12

C12 RNA is 1.1 kb bases long and is developmentally regulated. It is not expressed in root, leaf, ovule and flower. The C12 clone cross hybridizes with Pima, PD3 and Sea Island genomic DNAs, and is coded by one or two genes. The C12 clone has an insert of about 650 base pairs. The sequence is presented as SEQ ID NO: 3 below.

e. CKFB15A1-B8

B8 RNA is 1100 bases long and is developmentally regulated. It is not expressed in leaf, root, ovule and flower. Hybrid selection translation indicates that it encodes for a polypeptide of about 22 Kda. B8 cross hybridizes to Pima, PD3 and Sea Island genomic DNAs and is encoded by one or two genes. The B8 clone has an insert of about 700 bp, the sequence of which is SEQ ID NO: 4 below.

```
ACACACACAAGTAAAGCATTAGCAACCATAGCCATGGCTTCCTCACCAAAACTCTTCTCT
ATGTCTATCCTCTTCCTTTTTGCCCTCTTCTCCATGCAAATCCATGCTAGAGAGTACTTC
AGCAAATTCCCAAGAGTTAACATCAATGAGAAAGAGACAACAACCAGAGAGCAAAAGCAC
GAGACCTTCGTTCCCCAGACCACCCAAAAGCCAGAAGAACAAGAGCCAAGGTTCATTCCT
GAAACCCAAAATGGTTATGGCCTTTACGGCCACGAGTCAGGCTCAAGCCGGCCCAGTTTC
ACCACCAAAGAAACCTATGAACCCTATGTCACCCCTGTTAGATTCCACCCTGATGAGCCC
TATAACAGCATCCCCGAATCCTCCAACAATAAAGACACTTACTACTACAACAAGAATGCC
TACGAGTCCACTAAGCAGCAAAACTTGGGCGAGGCCATTTTCACCGAGAAAGGATGGAGC
ACCAAGGAAAACCAGAACAACAACTACTACAACGGCAACAATGGTTACAACAATGGCGAG
AAGCAAGGCATGAGCGATACTAGGTACTTGGAGAATGGAAAGTACTACTATGACGTCAAG
AGTGAGAACAACTATTATCCAAACCGGTTCGACAACTCAAGAGGGAGTTGCTTCGAGGAAC
GAGTTCAATGAGAATCGTTACAACAACATGGGAAGGTACCACCAGAACCAAGAGGAGTTC
GAGGAAAGCGAGGAAGAGTTCGAACCCTGATCACCTGTCGTACAGTATTTCTACATTTGA
TGTGTGATTTGTGAAGAACATCAAACAAAACAAGCACTGGCTTTAATATGATGATAAGTA
TTATGGTAATTAATTAATTGGCAAAAACAACAATGAAGCTAAAATTTTATTTATTGAGCC
TTGCGGTTAATTTCTTGTGATGATCTTTTTTTTTATTTTCTAATTATATATAGTTTCCTT
TGCTTTGAAATGCTAAAGGTTTG
``` b. CKFB15A1-All

This clone will be identified as A-11 to distinguish from the word "ALL." A-11 RNA is a low abundant message and is developmentally regulated. No A-11 RNA was detected in hybridization assays to leaf, flower, ovule and root.

A-11 cross hybridizes with Pima, PD3 and Sea Island genomic DNAs and is coded by one or two genes.

c. CKFB15A1-H6

H6 hybridizes to an RNA of 950 bases in length. It is developmentally regulated. H6 RNA was not detected in leaf, flower, ovule and root. The H6 clone also cross hybridizes to Pima, PD3 and Sea Island DNAs. It is coded by one or two genes in the cotton genome. The H6 clone had an insert of about 500 base pairs.

To obtain a full length cDNA clone, primer extension of H6 mRNA was conducted using an oligomer TCAATGGT-GTTTGTACTGGA and fiber cell mRNA using the protocol described by Dean et al., *Nucleic Acid Res.* 15 pp. 4655–4668 (1987). The primer extended product was then cloned into the Pst 1 site of dG-tailed pBR322. The complete sequence of H6 insert clone and the primer extended H6 (CKFBH6-10) were determined. Together, these two sequences make up the complete 913 base pair sequence of H6. This sequence, SEQ ID NO: 2 below, has a single long open reading frame of 713 nucleotides with an initiation codon at position 71. The nucleotide-derived amino acid composition shows a proline rich peptide (35% proline) of 214 amino acids. A total of five amino acids (alanine, proline, leucine, serine and valine) make up 74.3% of the protein, as indicated by Table II below. The sequence f. CKFB10-B12

The clone B12 cDNA is from RNA expressed only in fiber cells. The transcript size is 1 kilobase. The 727 base pair insert in B12 has been sequenced and is presented as SEQ ID NO: 5 below. The developmental pattern of expression of the clone showed that maximum concentration of B12 mRNA is present 10 to 20 days after anthesis. The concentration of B12 RNA in 24 day old cotton fiber cells is very low.

g. CKFB10-All

A-11 is also fiber specific. It has an insert size of 1 kb. Two mRNA transcripts from fiber cells hybridize to A-11 one 1.1 kb in size and the other 0.9 kb. The sequence for CKFB10-All is presented as SEQ ID NO: 6 below.

h. CKFB10-D7

The cDNA clone designated D7, from 10 day cotton fiber cells, hybridizes to an RNA of about 500 bases in length. It is not detected in ovule, leaf, flower or root RNA from cotton. The sequence of this cDNA clone is presented as SEQ ID NO: 7 below.

i. CKFB10-C2

This cDNA clone hybridizes to an mRNA highly expressed in cotton fiber cells but also detected as weakly present in petal tissues. The cDNA insert is 750 bp and hybridizes to an RNA of 1.1 kb. The sequence is listed as SEQ ID NO: 8 in the appendix.

j. CKFB10-C12

The cDNA clone C12 has an insert size of 700 base pairs. The transcript is expressed in fiber cells, but is also expressed at low levels in petal and pollen. The cDNA hybridizes to an mRNA of 1.1 kb. The sequence of CKFB10-C12 is shown in SEQ ID NO: 9 below.

k. CKFB10-C1

This clone hybridizes to a transcript of 450 base pairs in fiber cells. The cDNA also hybridizes very weakly to transcripts in petal and pollen. The insert size is also 450 base pairs. The sequence is SEQ ID NO: 10 below.

l. CKFB10-A8

This cDNA clone has an insert size of 450 base pairs and hybridizes to a 1 kb mRNA in fiber cells. The clone also exhibits weak hybridization to leaf and to petal RNA. The sequence of the insert is presented in SEQ ID NO: 11 in the sequence listing below.

m. CKFB10-A9

The cDNA clone A9 has an insert of 500 base pairs and hybridizes to an RNA of 750 bases in fiber cells. The clone exhibits weaker hybridization to RNAs from other tissues. The sequence is SEQ ID NO: 12 below.

n. CKFB10-D4

Clone D4 hybridizes strongly to 10 day fiber RNA and very weakly to petal RNA. Its transcript size is 500 bases and has an insert size of 455 bp. It is SEQ ID NO: 15 below.

o. CKFB10-B6

Clone B6 hybridizes to RNA of fiber. It also shows hybridization to leaf RNA (weak). It has an insert size of 1144 bp and transcript size of 1200 bases. It is SEQ ID NO: 16 below.

p. CKFB10-A12

CKFB10-A12 clone hybridizes to fiber RNA only. It has an insert size of 868 bp and hybridizes to a RNA of 900 bases. It is SEQ ID NO: 17 below.

q. CKFB15-E9

This clone hybridizes to fiber RNA strongly and weakly to petal RNA. It has an insert size of 1283 bp. The sequence is presented as SEQ ID NO: 18 below.

As will become apparent from the following, these cDNA clones can be used to obtain genomic clones, or cDNA coding sequences, so that plant transformation vectors can be constructed to transfer genes corresponding to these mRNAs into other fiber producing plants.

5) Identification of genomic clones

These cDNA fiber specific clones can be and have been used to identify genomic clones from genomic libraries of Coker, Pima, Sea Island, or Naked Seed cotton plants, and from other fiber-producing plants, such as Kapok, having homologous sequences. As described above, some of these cDNA clones have been found to cross-hybridize with RNAs from fiber cells of both Pima and Naked Seed cotton, indicating a sequence homology of these cDNAs with the genes of other species. Additionally, the five of the fiber-specific cDNA clones described above have been demonstrated to hybridize to genomic DNAs of Pima (cv. S6), Sea Island (cv. Barbados), and PD3 cotton. When the Southern blots of these cotton cultivars were compared with that of Coker C312, it was seen that identical size restriction fragments from these species hybridized to a given clone, demonstrating sequence conservation in different species. Thus, genomic clones corresponding to each of the fiber-specific cDNA clones can be identified in genomic libraries of Pima, Sea Island or PD3 cottons.

Similarly, hybridizations of the first five cDNA clones have been conducted with genomic DNA from a number of cotton species, including herbaceum, arboreum, anomalum, sturtianum, australe, nelsonii, thurberi, davidsonii, stocksii, somelense, longicalyx, and bickii. Many of these species are not grown commercially but grow wild in various locales. The DNA from all these cotton species showed hybridization with these five cDNA clones, indicating that these genes are conserved to a certain degree among cotton species. However, while all showed hybridization, there was variation in the size of the DNA fragments from the genomic DNA to which the cDNA clones hybridized suggesting structural differences among the corresponding genes in the various species. Similar results were found for at least one cDNA clone (E6) with genomic Kapok DNA. This supports the notion that these same cDNA clones can be used to identify and isolate corresponding fiber genes from a wide variety of fiber producing plants.

To create genomic clones, the EMBL-3 genomic library of Sea Island cotton was screened using cDNAs. This resulted in the identification of a number of phages that cross hybridized with these cDNA clones. These genomic clones are described below. The nomenclature is as follows, EMBL=Lambda vector; SI=Sea Island; E6=cDNA clone that hybridizes to genomic clone; the last numbers or characters correspond to different genomic clones from a given library. The following fragment sizes are approximate.

(a) EMBLSIE6-1

Insert DNA size is about 15 Kbs. A 6.0 Kb Sal I restriction fragment hybridizes to E6 cDNA.

(b) EMBLSIE6-2

Insert size is about 15 Kbs. A 9.5 Kb Sal I fragment hybridizes to E6 cDNA.

(c) EMBLSIE6-3

Insert size is about 15 Kb. A 4.8 Kb Sal I fragment hybridizes to E6 cDNA.

(d) EMBLSIH6-1, EMBLSIH6-2, EMBLSIH6-4 and EMBLSIH6-6. Insert size in all four independent phages are about 15 Kb each. In every case a Pst I fragment of 5.8 Kb hybridizes to cDNA clone H6.

Phages that hybridize to CKFB15A1-C12 and CKFB15A1-B8 have also been identified.

Similarly the *Cebia pentandra* (Kapok) genomic library was screened with the cDNA clone E6 and four hybridizing phages were identified.

These results indicated that these five probes can be used to identify genomic clones from other cotton species, and even from other fiber producing plants.

Characterization of genomic clones (In General)

Once the DNA has been purified from the phage genomic clones (Ausubel et al., PP. 1.10.1 to 1.13.6) the insert DNAs (10 to 15 Kbs) may be characterized in terms of their restriction maps (supra, PP. 3.1.1 to 3.3.2). The different restriction fragments may be separated on agarose gels and Southern blotted. The blots may then be hybridized to cDNA probes. This procedure will enable one to identify smaller fragments (about 5 to 10 Kb) that contains the homologous cDNA sequence. This fragment may then be subcloned (supra, 3.16.1 to 3.16.11) into plasmid vectors such as pGEM5zf (Promega, Madison) or Bluescript SK, KS (Stratagene, Calif.). All further manipulations such as promoter identifications, transcription maps and gene size determinations may then be done using the subclones.

Mapping the gene transcripts by nuclease protection may also be done. Single stranded DNA probes may be generated from the Bluescript subclones and hybridized to poly(A)⁺ RNA from fiber cells. The hybridized portions that are protected from nuclease action will be determined as described by Calzone, F. J. et al. in *Methods in Enzymology*, Vol. 152 (Eds. Berger, S. L. and Kimmel, A. R.) pp. 611 to 629. Furthermore, mapping the 5' termini by cDNA primer extension is also described (supra pp. 629 to 632). These strategies will determine the size of the gene, as well as precise boundaries of the gene transcript, or coding region for the fiber gene, in the subclone. That portion of the DNA may then be sequenced if desired.

It is then possible to use a beta glucuronidase expression system to identify DNA sequences needed for the transcription of the genes. In this system, an *E. coli* beta-glucuronidase (GUS) coding region is fused with a plant DNA containing a promoter and the construct is introduced into plant cells. The enzymatic activity is then measured in cells using 5-bromo-4-chloro-3-indolyl glucuronide (X-Glu). The GUS system is described by Jefferson, R. A. et al., *Proc. Natl. Acad. Sci. USA*, 83, 8447–8451 (1986). A GUS fusion construct may be used to identify cotton promoters. This may be done as follows: First the transcription start site of the mRNA is determined by primer extension method as described by Calzone et al. (supra). The subcloned gene fragment and a short restriction fragment or an oligomer at the 5' end is used in the primer extension. A beta glucuronidase (GUS) coding sequence along with necessary termination signals, as well a 5' leader sequences, may be used with an up stream 2 to 3 Kb DNA fragment from the transcription or translation start site. The beta glucuronidase sequence is already readily publicly available (ATCC 67641). It has been demonstrated that a GUS gene construct with a Cauliflower mosaic virus 35 promoter (CaMV35s) promoter is functional in fiber cells, and thus when this construct is introduced through particle bombardment (described by McCabe et al., supra) into the epidermal cells of ovule tissue grown in tissue culture according to the method described by Beasley, C. A., in *Plant Cell Tissue and Organ Culture*, (Eds Reinert, J. and Bajaj, Y. P. S.), pp. 160–178 (1977), GUS activity is observed. If the construct containing an unknown DNA is found to be active in expressing GUS, then it can be concluded that the DNA fragment contains a promoter that directs the expression of GUS gene. Using the Bluescript subclone and exonuclease/ mung bean deletion procedure, in which a series of clones with differing lengths of the 5' fragment are generated, one can identify minimum lengths of 5' DNA necessary to express the gene in fiber cells. These types of procedures will enable one to identify promoters from all genomic clones. Based on this knowledge, one can construct various developmentally regulated expression vectors containing fiber genes of interest and introduce them into plants.

Also one can construct various chimeric genes to alter expression of genes by matching promoters or other regulatory elements.

Characterization of Cotton E6 Gene

Three of the genomic DNA fragments containing sequences complementary to the E6 cDNA are identified above. The insert in the phage EMBLSIE6-2 has been characterized. It has a 15 kb insert. Within that insert, a 9.5 kb Sal I digest fragment hybridizes to E6 cDNA. This 9.5 kb fragment was subcloned into a phagemid vector, Bluescript SK+ (Stratagene).

The subcloning of DNA inserts into plasmids and phagemids were done using the following protocol. After linearization of the vector by Sal I digestion, the fragment was treated with calf intestinal Alkaline Phosphatase (Boehringer Mannheim) according to the protocol of the manufacturer, to prevent self-ligation. The phosphatase was inactivated by heating and phenol:chloroform extraction. The gel-purified, de-phophorylated vector was then further purified and concentrated by passing through an Elutip-d column (Schleicher & Schuell). The vector and the insert DNAs were ligated using T4 DNA ligase (BRL). The ligation conditions were by the manufacturer. The ligated DNA was then transformed into *E. coli* strain XL-1 Blue (Stratagene).

The recombinant strains selected on the basis of blue/white colony selection on X-gal, IPTG (5-bromo-4-chloro-3-indoyl-beta-D-galactopyranoside; isopropyl-beta-thio-glactophyranoside) plates were then analyzed by SDS-agarose gel electrophoresis by the method of Sekar, *Biotechniques*, 5 pp 11–13 (1987). The clones were characterized by restriction mapping and Southern analysis. Further subcloning of smaller restriction fragments was done as needed. These techniques permitted the determination of the approximate boundaries of the given gene.

Following this protocol, the DNA insert from genomic clone EMBLSIE6-2 was subcloned into phagemid vector Bluescript SK+. This phagemid construction contains one Hind III site in the inserted DNA, 3' to the E6 gene, and one Hind III site in the polylinker of the vector. The plasmid was digested with Hind III and the largest fragment, containing the E6 gene, was gel purified. After ligation using T4 DNA ligase and transformation using XL-1 Blue cells, a shorter fragment containing the E6 gene was obtained. The complete sequence for the E6 gene, 1672 base pairs, in pSKSIE6-2AH3 has been obtained and is presented as SEQ ID NO: 13 below.

Sequence comparison of the Coker 312 and Sea Island E6 sequences revealed significant sequence homology. The first (5') 276 base pairs are identical, followed by a 24 base pair region in Sea Island missing in the Coker cDNA. An S1 nuclease protection analysis of the Sea Island genomic clone with mRNA from Coker C312 suggested that there is at least one intron, and perhaps two, in the Sea Island E6 gene. Alternatively it is possible that the 24 bp region in Sea Island gene is a coding region and is missing in Coker variety. The remaining sequence from 277 to 752 are identical in both the Coker cDNA and the Sea Island gene. Thus the primary structure of this gene in these two varieties are remarkably similar. Analysis of the amino acid sequence of the Coker E6 cDNA (Table 1) reveals a relatively large number (8.8%) of tyrosine residues. Previous studies of plant primary cell wall proteins have suggested a structural role for tyrosine containing peptides through the formation of isodityrosine intermolecular or intramolecular cross linkages. The isodityrosine, a phenolic amino acid derivative formed by covalent linkage of two tyrosine residues, has been found in plant primary cell walls, Fry, *Biochem J*. 204, pp 449–455 (1982), Epstein et al, *Phyto. Chem.* 23, pp. 1241–1246 (1984). The cross linkages between cell wall proteins through isodityrosine has also been postulated to result in the rigidification of cell walls and to lead to the suppression of growth, Lamport, *Annual Rev. Plant Physiol.*, 21, pp. 235–270 (1970), Fry, *Plaanta*, 146, pp. 343–351 (1979). The large number of tyrosine residues in the E6 protein suggests that it may form isodityrosine linkages and this may be a cell wall structural protein. In cotton fiber cells, the primary cell wall determines the length and outer diameter of the cell. If the primary cell wall is too rigid, it can restrict the deposition of cellulose during secondary wall formation, since the cell cannot expand. The secondary wall determines the strength of the fiber. Hence the primary cell wall proteins are related to fiber strength.

The formation of isodityrosine can be regulated by two possible mechanisms, one being the enzyme which catalyzes the formation and, the other being the amount of tyrosine present for reaction. To test to see how the relative abundance of E6 correlated with fiber strength, RNA from different cotton plants, Pima S6, naked seed (NiNi), and from weak and strong fiber were analyzed. The findings indicated that stronger fiber had reduced levels of E6 expression while the inverse was true for weaker fibers. This relation suggests that fiber strength can be further increased by diminishing production of the E6 gene in cotton cells.

To further characterize the location of the E6 protein in fiber cells, antibodies were prepared for epitopes corresponding to the deduced amino acid sequence. For the E6 study, a 22 residue peptide was prepared by Immuno-Dynamics (LaJolla, Calif.) having the following sequence.

Cys-Thr-Thr-Gln.-Lys-Pro-Glu-Glu-Gln-Glu-Pro-Arg-Phe-Ile-Pro-Glu-Thr-Gln-Asn-Gly-Try-Gly

Antibodies to this peptide were produced in rabbits. The antibodies were labelled with gold and reacted with cotton fiber sections. Under phase contrast electron microscopy, the antibodies were found in cotton fiber cell walls.

8) Characterization of Cotton H6 Gene

The 13 kb DNA insert (Sal I fragment) from the clone EMBLSIH6-4 was subcloned into Bluescript SK+ vector and designated pSKSIH6-4. After identifying the cDNA hybridizing region in pSKSIH6-4, the H6 gene was further subcloned by digesting the plasmid with Eco RI, purifying the fragments, and religating the fragments with the Bluescript vector and the H6 gene. The resulting plasmid, designated pSIH6-4R1, contains the H6 gene. The complete sequence of H6 was determined.

Sequence comparison of the H6 gene with H6 cDNA reveal that the gene contains a single intron (582 bp) also plasmid pSIH6-4R1 contains a 300 base pair fragment upstream from the initiation codon of the H6 gene. Digestion with the enzyme Fsp I releases this fragment, useful as a tissue specific promoter, together with 250 base pair of vector sequence.

The H6 gene product was localized by antibody study similar to that done for E6. The peptide synthesized had the following sequence:

Cys-Ala-Pro-Thr-Leu-Gly-Ala-Ala-Thr-Pro-Gly-Pro-Ala-Gly-Thr-Asp-Thr-Ser-Gly-Ala-Asn

The antibody study indicated that the H6 protein is also located in the cotton fiber cell wall.

9) Characterization of Kapok E6 Gene

An EMBL-3 genomic library of Kapok (*Cebia pentandra*) was screened using the insert of CKFB15Al-E6. Four hybridizing phages were identified. One of the phage inserts was subcloned into the Sal I site of the Bluescript Sk+ vector. The clone, designated pSKCPE6-3A, was characterized by restriction analysis and Southern blotting. A Sal I-Eco RV fragment of 4.8 kb that hybridized to CKFB15Al-E6 was identified. This fragment was subcloned into the Sal I and Eco RV site of the Bluescript vector, resulting in a clone designated pSKCPE6-RV. Sequence analysis of the 1618 base pair region that includes the E6 gene has been completed. A comparison of the cotton E6 cDNA sequence to the Kapok E6 gene revealed a homology of 84.3%. This level of homology indicates very similar function of the gene. The sequence of Kapok E6 is listed as SEQ ID NO: 14 below.

10) Potential Types of Expression vectors a) Positive Strand Full Length cDNAs

Thus the identified fiber-specific cDNA clones can be used as probes to select full length cDNA clones from the cDNA library. Alternatively, it may be possible to hybrid select RNA and clone it as described by Jagus, R., *Methods in Enzymology*, 152:567–572 (1987). Any one of these procedures will result in the identification of full length clones of fiber specific genes.

The full length clones can then be used to construct expression vectors for expression in cotton plants. However, a fiber-specific promoter would be helpful for this purpose. Such a promoter can be identified, as described above, for use in this procedure.

b) Modified coding region cDNAs

Specific changes in the DNA sequences can affect functioning of corresponding proteins. This property can be utilized to create novel proteins in a transgenic plant. All the fiber specific clones that we have identified can therefore be used to do general or site-specific mutagenesis to create new proteins. Full length cDNA clones will be identified as described above. Oligonucleotide-directed mutagenesis, mutagenesis with degenerate oligonucleotides, region specific mutagenesis or linker scanning mutagenesis can be performed on these clones. The methodology required for this is well known to those skilled in the art. (*Current Protocols:* Ausubel et al., pp. 8.0.3 to 8.4.7 supra). This may result in the synthesis of proteins with altered properties such as changes in substrate affinities, and stability.

c) Negative Strand cDNAs

Both full length or partial cDNA clones can be used to construct expression vectors in such a manner that upon transcription, an RNA is produced that is complementary to endogenous messenger RNA. This will result in the hybrid formation of RNA-antiRNA and will inhibit the level of expression of that message. As with the positive strand vector, only a fiber-specific promoter is desirable. In this way, undesired genes in a given cotton cultivar can be controlled or suppressed to increase or alter fiber quality.

11) Antisense construct from E6

The construction of this plasmid is illustrated in FIG. 1.

As the first step in creating an antisense construct, the coding region of the E6 plasmid was selectively amplified using PCR. The two primers used were EJ43 and MEJ5, which has the following sequences.

EJ43-5'-ATGCGCAAGCTTTGGCTTCCTCAC-CAAAAC-3' MEJ5-5'-GTCGACCATGGGTTC-GAACTCTTCCTC-3'

Using these primers, the coding region in pSKSIE6-2AH3 was amplified by PCR reaction. The primer EJ43 contains a Hind III site while the primer MEJ5 contains an Nco I site. The amplified product of the PCR reaction was then digested with both Hind III and Nco I and gel purified. Similarly, pSKSIE6-2AH3 was digested with Hind III and Nco I and the products separated by agarose gel electrophoresis. The 8.8 kb fragment containing the vector and promoter was electroeluted, purified and then ligated to the PCR product. The ligated plasmids were transformed into *E. coli* strain RR1 cells, and recombinant clones were selected by the SDS-Sekar method described above. The resulting plasmid was then digested with Bam HI and dephophorylated with calf intestinal alkaline phosphatase.

To obtain a polyadenylation region, an available plasmid, pCMC2117, was digested with Bam HI and a 280 base pair fragment containing the nopaline synthase polyadenylation signal was purified by gel electrophoresis. This fragment was then ligated into the Bam HI site of the dephophorylated construct containing the antisense E6. To incorporate a useful marker gene into the construct, a gene for beta-glucuronidase (GUS) driven by the *Arabidopsis thaliana* chlorophyll a/b binding protein promoter (Cab) was chosen. The sequence of this promoter has been published by Ha and An, *Proc. Natl. Acad. Sci. USA*, 85 pp 8017–8021 (1988). The promoter was isolated from Arabidopsis DNA using PCR with the following two primers.

(1) AAGCTTCTCGAGAGAGATCTATTCGTATACGT (2) AAGCTTCCATGGTAAGGTTGAGTAGTGCAGCA

Following the PCR procedure using these primers, an amplified 320 base pair DNA fragment was isolated. This DNA was digested with Xho I and Nco I and cloned into the plasmid pCMC2117, which had been digested with Nco I and Xho I.

To verify the promoter activity of the Cab-2117 sequence, the construct thus assembled was introduced into cotton hypocotyles by accelerated particles. The presence of areas within the treated hypocotyles exhibiting GUS gene activity verified the promoter function of the fragment.

To excise the Cab-GUS gene from its plasmid, the construct was digested with Xho I and Sal I, and a 2.5 kb fragment was purified by agarose electrophoresis and electroelution. The DNA was then blunt ended by treatment with T4 polymerase reaction and Not I linkers were added as described in Maniatis, supra. After digestion with Not I and gel purification, the fragment was ligated to the antisense construct at its Not I site.

The resulting plasmid, designated pAntiE6/Cab-GUS, has been replicated and introduced into cotton tissues by particle acceleration. The regeneration of the tissues into plants is in progress.

It is expected that the resultant plants will have a reduced level of expression of the E6 protein. It is therefore reasonable to expect the plants to have cotton fiber of increased strength.

12) Transformation of plants

The most common methodology used for the transformation of cells of dicot plant species involves the use of the plant pathogen *Agrobacterium tumefaciens*. *A. tumefaciens* harbors a plasmid, referred to as the tumor-inducing or Ti plasmid, which has the natural ability to transfer a segment of itself, referred to as the T-DNA (transfer-DNA), into the genome of infected plant cells. Wild-type *A. tumefaciens* use this ability to genetically transform infected cells of plants so that the plant cells become tumorous, and also synthesize one of a series of compounds, known as opines, which can be metabolized by the infecting *A. tumefaciens*. It has been found by several investigators that by removing the bulk of the T-DNA from the Ti plasmid harbored by *A. tumefaciens*, and by replacing that T-DNA with a foreign gene construction, the Agrobacterium can transform infected plant cells with the foreign gene in such a fashion that the resultant cells are not tumorous, as plant cells infected with wild-type *A. tumefaciens* normally are. The foreign gene construction is then included in the cells of a whole plant regenerated from the transformed cells and is then inherited in a simple Mendelian manner. The construction can thus be treated as any inheritable trait for crop breeding purposes.

The transformation and regeneration of cotton plants by Agrobacterium transformation has been achieved and reported. Umbeck et al. (supra) and Firoozabady et al. (supra). Other methods of plant transformation, such as transformation by accelerated particle carried DNA, are now available (McCabe et al. supra). In any event, once the creation and assembly of plant expression vectors including fiber specific gene sequences is accomplished, the transformation and regeneration of cotton plants with these expression vectors is within the ability of one of ordinary skill in plant genetic engineering, and is not dependent on the method of transformation.

13) General Use of Clones

It has been demonstrated above that the cDNA clones described above have several uses. They may be used as hybridization probes to identify genomic clones of cotton fiber genes so that the native fiber genes can be cloned, reproduced, and studied. They may also be used to identify homologous genes from other fiber producing plants, as exemplified with Kapok above. The cDNA clones may be used to construct coding sequences, either directly or indirectly through the identification of genomic clones, to construct expression systems to express fiber genes in cotton plants not normally having the genes. The cDNA clones can be used, as illustrated above, to construct antisense constructs to lessen or inhibit expression of an endogenous gene. Also, the clones may be used to identify fiber specific promoters, for use with these or other genes to express genetic products specifically in fiber cells. All these possibilities become reasonable from the identification of these clones, using only techniques known to those of ordinary skill in the art.

14) Deposit

The cDNA clones referenced above have been deposited under the terms of the Budapest Treaty with the American Type Culture Collection, Rockville, Md. U.S.A. (ATCC). Availability of these clones is not to be construed as a license to practice the invention in contravention of any rights granted in accordance with the patent laws of any government.

These cDNA clones may readily be used, as described above, to generate genomic clones from cotton of any species. While the isolation of these cDNA clones of fiber genes was difficult, the isolation of genomic clones using these cDNA clones is expeditious and readily replicable by one of ordinary skill without undue experimentation. The procedures to use those genomic clones to create gene constructions to transform cotton plants, while laborious, are well documented and reproducible by those skilled in the field.

The cDNA clones have been deposited both with the ATCC and the Master Culture Collection of Cetus Corporation, Emeryville, Calif., U.S.A. The clones have been assigned the following accession numbers:

| cDNA clone | CMCC Accession No. | ATCC Accession No. |
| --- | --- | --- |
| CKFB15A1-E6 | 3432 | ---67809 |
| CKFB15A1-A11 | 3429 | ---67806 |
| CKFB15A1-H6 | 3433 | ---67810 |
| CKFB15A1-C12 | 3431 | ---67808 |
| CKFB15A1-B8 | 3430 | ---67807 |

It is to be understood that all sequence and size data presented here about nucleotide molecules is approximate and, although presented as best understood at the present time, may be subject to some variation.

It is to be understood that the present invention is not confined to the particular construction and arrangement herein illustrated and described, but embraces such modified forms thereof as come within the scope of the following claims.

The work described below demonstrates the modification of transgenic cotton fiber in a specific, measurable manner. The cDNAs or genes were used both in constructs with an "antisense" orientation to shut down or to reduce corresponding gene expression and in constructs with a "sense" orientation to demonstrate over-expression of the message.

Construction of Antisense Genes

Antisense E6 Genes (AS-52 and AS-58). The 5'-end of coding region of the E6 gene (described above) contains an Nco site where translation initiation occurs. At the 3'-end of the gene there is a Hind III site. These two sites were used to clone a modified E6 gene so that an antisense RNA is produced on tnranscription. This was accomplished by deleting the Nco site from the 5'-end coding region and inserting a Hind III site in its place. The 3'-end was similarly modified by inserting an Nco site. The coding region of E6 gene was amplified by PCR using two primers and cotton genomic DNA clone SKSIE6-2AH3. (Saiki et al., *Science*, 239; 487–491, 1988). The two PCR primers we used were: 5'-ATG CGC AAG CTT TGG CTT CCT CAC CAA AAC-3' (called MEJ4, SEQ ID NO: 19) and 5'-GTC GAC CAT GGG TTC GAA CTC TTC CTC-3' (called MEJ-5, SEQ ID NO: 20).

Primer MEJ-4 contains a Hind III site and primer MEJ-5 contains an Nco site. Thus, upon amplification using these primers the E6 coding region had a modified 5'—and 3'—end. The amplified DNA was digested with Nco and Hind III and gel purified.

Figure 2:
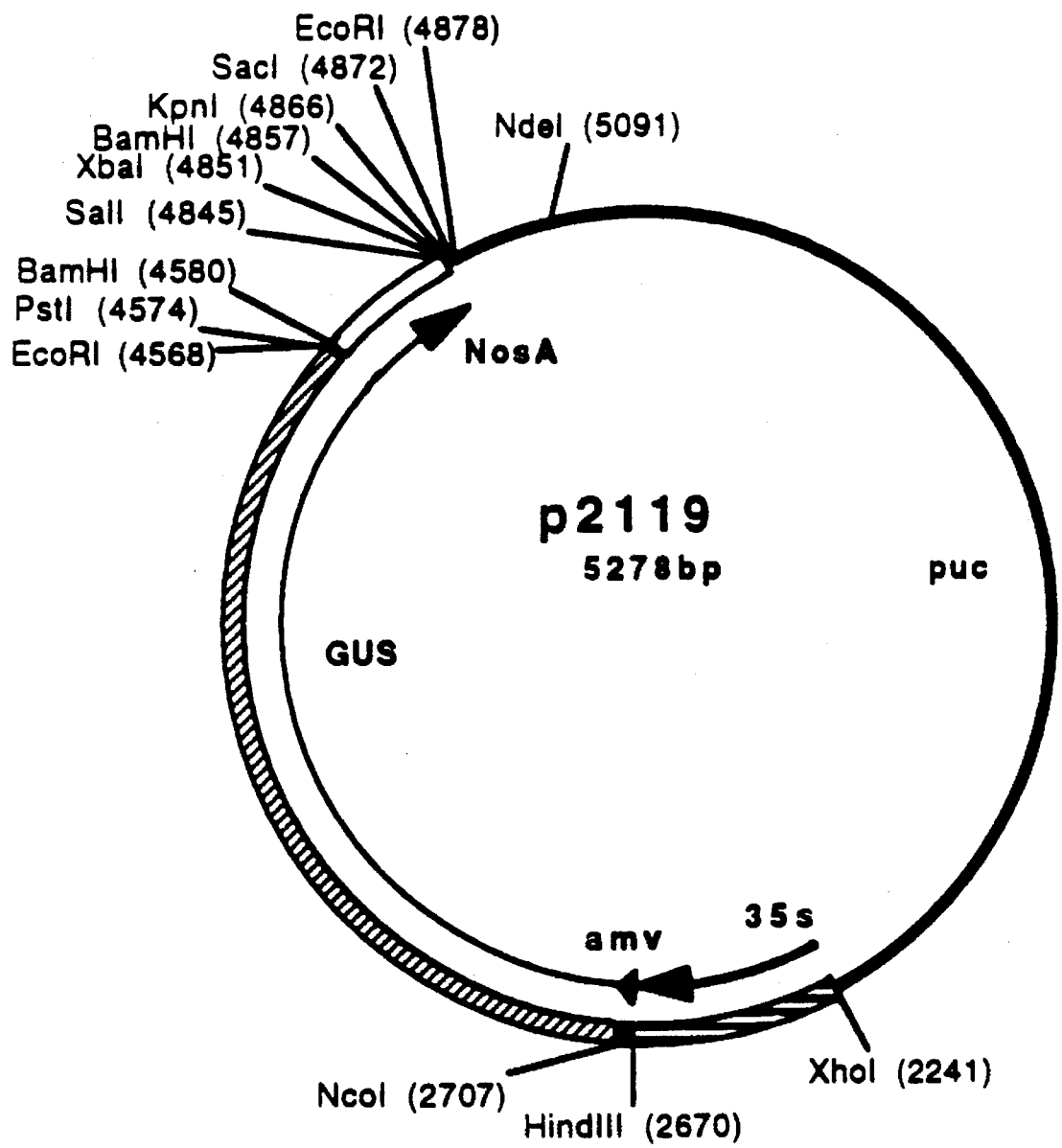
FIG. 2 is a diagram of plasmid 2119.

Similarly, SKSIE6-2AH3 was digested with Nco and Hind III and gel purified to remove the 1.5 kb coding region. The remaining E6 promoter along with the SK vector was then ligated with the above-described PCR product. Recombinant clones carrying the E6 antisense gene were then detected by Sekar gel electrophoresis. A Nos-poly-(A) signal was added at a Bam HI site and the orientation determined. Finally, a Gus gene connected to the CaMV 35S promoter was ligated at Xho I site as a Xho/Sal fragment from plasmid 2119 (which contains the Gus gene) to generate plasmid AS-52. (FIG. 2 shows a map of plasmid 2119.) Therefore, AS-52 contained an E6 promoter (fiber-specific), an antisense E6 message, and a Gus gene connected to the CaMV 35S promoter.

A second antisense E6 gene containing a 35S promoter was constructed as follows. The 35S promoter from plasmid 2119 was excised as an Xho/Nco fragment and gel purified. Similarly plasmid AS-52 (before the addition of Gus gene, see above) was digested with Xho/Nco to remove the E6-2A promoter and the vector fragment purified. The 35S fragment was then ligated to the vector in place of the E6-2A promoter. A Gus gene was added at the Not site to generate AS-58. Therefore, AS-58 contains an E6 antisense gene with a 35S promoter, Antisense H6 Gene (Plasmids AS-53 and AS-62). The H6 gene (described above) contains a 71 bp untranslated 5' leader followed by an exon, which is then interrupted by an 583 bp intron. We used two PCR primers to amplify the 5'-end of he gene: 5'-ATC TTA AGC TTT CAC ACG GGT TGT GGC G-3' (called MEJ42, SEQ ID NO: 21) and 5'-ACA ATC CAT GGG TGT CAG TTC CAG CTG G3' (called MEJ43, SEQ ID NO: 22). MEJ 42 contains a Hind III site and MEJ 43 contains a Nco site. PCR amplification from genomic clone SKSIH6-4RI resulted in a 600 bp fragment that was purified and then digested with Hind and Nco. The amplified DNA fragment was then cloned into the E6 promoter vector (SKSIE6-2AH3) as described for the construction of AS-52. A poly(A) addition signal was then added. Transcription from this plasmid results in the production of an antisense H6 RNA. As described above, a 35S-Gus marker gene was added at the Xho I site as a Xho/Sal fragment to create AS-53.

A second H6 gene construction was made using the 35S promoter. I used plasmid 2119 as a 35S promoter vector. The H6 insert from AS-53 was excised as an Nco/Sac fragment and gel purified. Plasmid 2119 (which contains 35S Gus gene) was digested with Nco/Sac to remove the Gus coding region. The large vector fragment was also gel purified. The H6 gene was then ligated into the 2119 vector at the Nco/Sac site. A heat-shock promoter/Gus gene construct was then added as an Xho/Sal fragment at the Sal site to generate AS-62.

Antisense B12/AS-55). We also constructed antisense constructs from additional fiber-specific genes. One of these constructs was for B12 cDNA, which we had previously determined to be fiber-specific. B12 cDNA is described above.

Similar cloning steps to those used above were used to generate plasmid AS-55, which contains an antisense gene for B12. The cDNA insert from CKFB10-B12 was excised and cloned into the SKSIE6-2AH3 vector. The cDNA insert was excised as a Pst I fragment and ligated into a modified SK vector (SK-Nco) at the pst I site. The SK+ vector was digested with Sma I and Nco linkers were added. The new SK vector containing the Nco site is referred as SK-Nco vector. The orientation of the B12 cDNA insert in SK-Nco vector was determined and plasmids carrying an insert in the antisense orientation in relation to Nco site were digested with Nco and Hind III. Nco and Hind III sites flank the Pst I site in Sk-Nco vector. The liberated cDNA insert was gel purified and ligated into Nco/Hind III site of SKSIE6-2A H3 vector as described above for AS-52. A Nos poly(A) signal and marker gene Gus were added. This plasmid was called AS-55.

Figure 3:
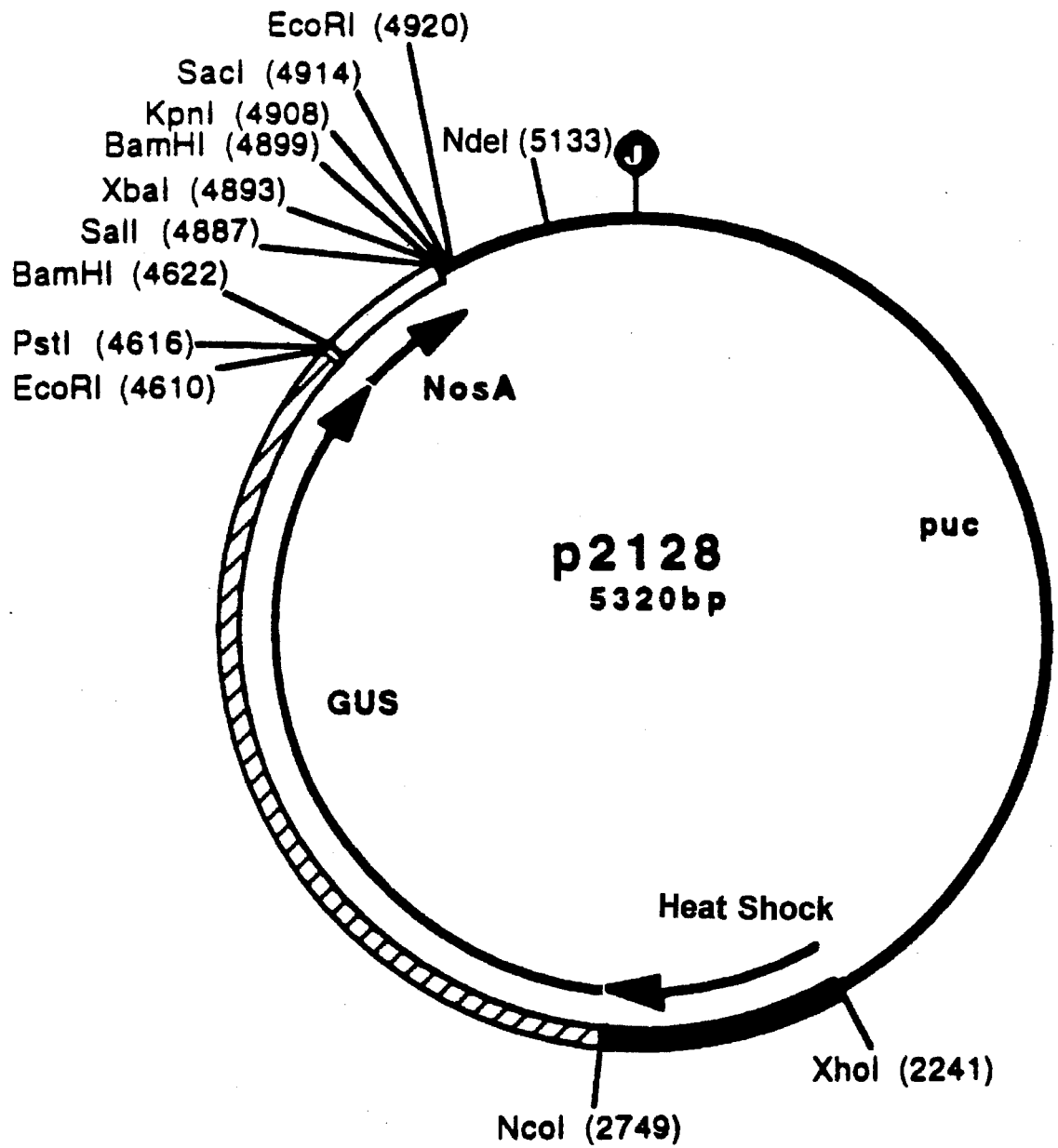
FIG. 3 is a diagram of plasmid 2228.

Construction of B12 antisense gene/CaMV 35S promoter (AS-61). We then constructed a second set of plasmids with the CaMV 35S promoter. The cDNA insert of AS-55 was excised as a Nco/Sac fragment and purified. Plasmid 2119 was digested with Nco and Sac and the large vector fragment was purified and ligated to the antisense B12 cDNA insert. A heat shock promoter/Gus gene construct was then added to the Xho site as a Xho/Sal fragment to generate plasmid AS-61. FIG. 3 shows a map of a plasmid (p2128) containing the heat shock promoter and the Gus gene.

Construction of E6 Promoter-H6 Gene Construct (MS 600). In addition to the antisense gene constructions, we also attempted to over-express some fiber-specific genes to investigate the effect on fiber properties. This was accomplished by ligating a strong fiber-specific promoter to the gene in question. An example is the construction of H6 gene, described below. The characteristics of the nucleotide derived amino acid sequence of H6 gene suggest that it is a cell wall protein. Since cotton fiber derives its strength from both primary and secondary cell walls, we examined the implication of over-expression of the H6 gene product in terms of fiber properties.

Figure 4:
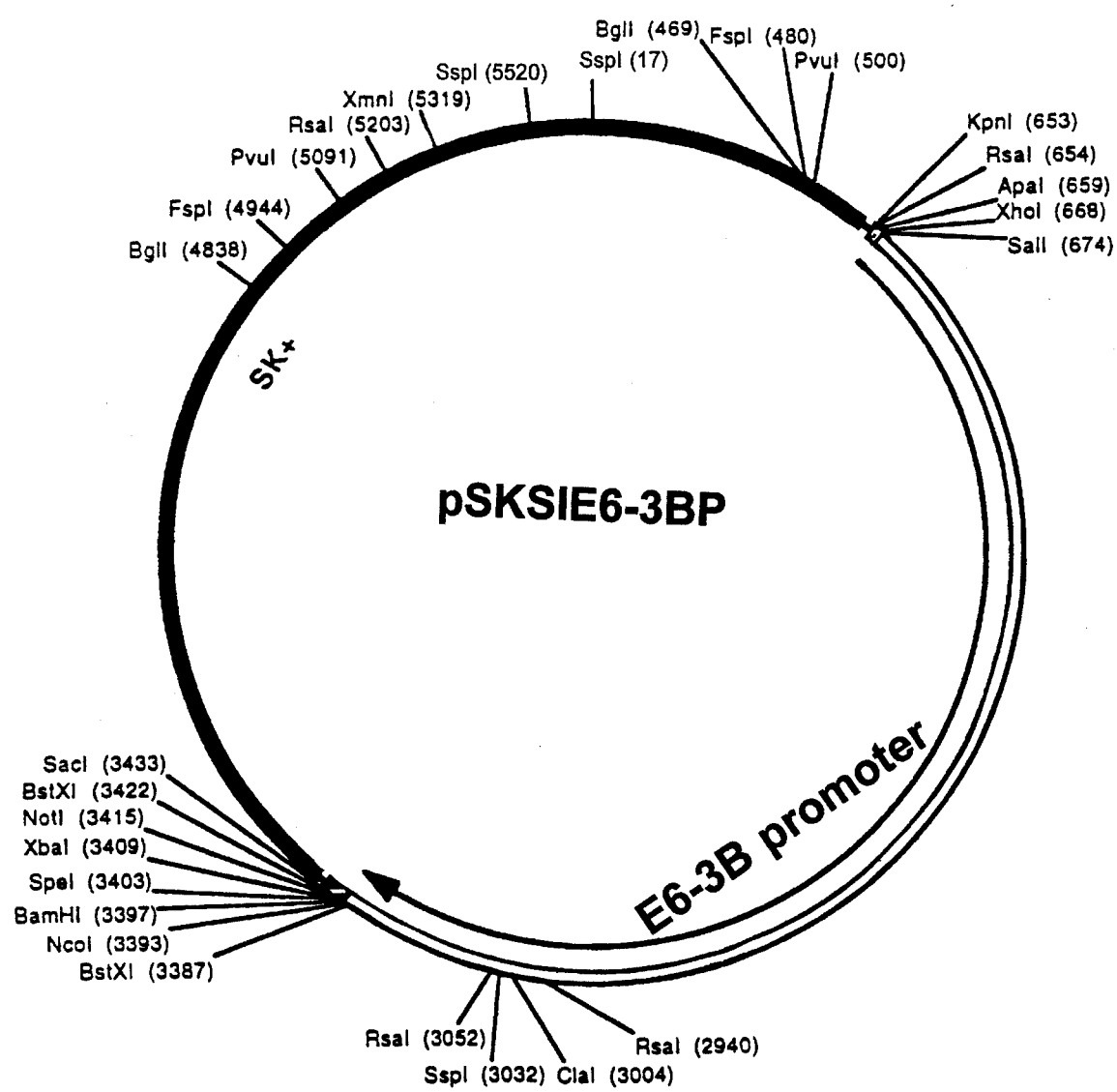
FIG. 4 is a diagram of a plasmid carrying the E6-3B promoter.

The cotton genome contains more than one E6 gene. We have identified and characterized two E6 genes. The pSKSIE6-2A promoter has already been described herein. A second gene, contained in a 5.1 kb Sal-I fragment, was cloned into the SK vector and is referred to as pSKSIE6-3B. We identified the promoter of the E6-3B gene as being contained within a 2.7 kb Sal/Nco fragment. The map of a vector containing the 2.7 kb E6-3B promoter is shown in attached FIG. 4 and is referred to as From our studies on various fiber promoters using transient Gus gene expression, we had concluded that E6 is probably one of the stronger promoters in fiber compared to our other characterized promoters. Therefore, we decided to combine the E6 promoter with the H6 gene. The H6 gene was excised as a 1.9 kb fragment from SKSIH6-4RI by digestion with Fsp and Eco RI. The gel-purified fragment was then blunt-ended with T4 polymerase reaction. Xba linkers were added. The H6 gene (with linkers) was then cloned into the Xba I site of vector pSKSIE6-3B, which contained the E6 promoter, and clones containing insert in the correct orientation were selected. The insert in these plasmids is in such an orientation in relation to the E6 promoter vector that upon transcription H6 RNA will be synthesized. Addition of 35S Gus gene then generated plasmid MS 600.

Construction of Kapok E6 gene (KPO4). Kapok (Silk cotton wood) produces a fiber that is very fine (low micronaire). It is desirable to have low micronaire in upland cotton provided other properties are not affected. Therefore, we examined the effect of expressing a Kapok gene in fiber. The kapok gene, SKCPE6-3A-RV (described above) cross-hybridizes with cotton E6 gene. A Gus marker gene as a Xho/Sal fragment was added to the above plasmid to create KPO4.

Transformation

Cotton Transformation: Epidermal and Germline Transformants. The protocol for the generation of transgenic cotton developed by McCabe and Martinell (Bio/Technol. 11: 596–598, 1993) allowed us to generate germline or non-germline (epidermal) transformants in DP50 cotton for all the constructs described above. In germline transformants, the transgene is passed on to progeny in a Mendelian fashion. In epidermal transformants the progeny are not transgenic. Therefore, the epidermal plant has to be propagated vegetatively (McCabe and Martinell, supra). However, because cotton fiber is derived from maternal epidermal tissue, epidermal transgenic plants are suitable for testing effect of transgenes on fiber properties. (We have monitored transgene expression in vegetatively propagated epidermal transformants for over three years and have shown stable expression of the transgene.)

The frequency of generation of epidermal transformants is an order of magnitude higher than that of germline transformants. Thus, in a given experiment we generate a large number of epidermal transformants that can be used for fiber modification studies. The generation of epidermal transformants also lends itself to testing the effect of the new gene on the fiber properties versus the nontransgenic germ plasm.

As seen in Table 1, below, there are variations in the fiber properties from plants of the same cultivar. In DP 50 the maximum strength we have seen among 35 plants grown under identical conditions is 20.6 gm/tex. The minimum is 17.5 gm/tex. We assume that the individual germplasm is responsible for this variation. In an epidermal transformant, the fiber properties reflect the effect of transgenes while the progeny of that plant reflects the effect of its original germplasm. Thus, if one observes increased fiber strength in a epidermal plant, by examining the progeny one can decipher whether the increased strength is due to transgene or due its inherent germplasm.

Fiber Property Measurements

Strength. Cotton fiber strength can be measured in a number of ways. The most common measurement, and the method we used, is that of the fiber bundle strength. The fiber bundle strength measurements are made with a ⅛ inch spacer between the clamp jaws (⅛ inch gauge) of Stelometer or the Motion Control High Volume Instrument (HVI). The results are given in grams per tex. A tex unit is equal to the weight in grams of 1,000 meters of the material. Results of Stelometer ⅛ inch gauge tests are calculated by the use of the following formula:

$$\text{grams per tex (g/tex)} = \frac{\text{breaking load (kg)} \times 15}{\text{bundle weight (mg)}}$$

The results are adjusted to Presssley level by the use of calibration cottons.

Length. There are a wide range of fiber lengths within a bale of cotton. Comb sorters provide a way of sorting the fibers into different length groups, usually 1/16 of an inch intervals. Instruments such as fibrograph and HVI system were used to compute length in terms of "Mean" and "Upper Half Mean" length. The mean is the average length of all fibers and the upper half mean (UHM) is the average length of longer half of the fiber distribution. The fibrograph measures length in span lengths at a given percentage point. The 2.5% span length is the span length that agrees best with classers staple and indicates that 2.5% of the fibers are of this or longer. Table 1 shows the normal 2.5% span length of various cotton cultivars.

Micronaire. Fiber fineness and maturity in combination can be determined by the micronaire test. This is an instrument test which measures the resistance of a plug of cotton to air flow. From 47 to 52 grains of cotton are placed in the instrument specimen holder and compressed to a fixed volume. Air at a know pressure is forced through the specimen and the amount of flow is indicated by a direct reading scale. Readings obtained are relative measure of either the weight per unit length or cross sectional size of the fibers. Because the instrument measures may differ from the actual weight per inch depending upon the fiber characteristics of the sample, the results are reported in terms of "micronaire reading" instead of micrograms per inch. The air flow reacts to the surface area of the fibers presented to it. Since both small diameter mature fiber and a large diameter thin walled fiber will present a relatively high surface area, the test will indicate both maturity and fineness.

The fiber diameter within a given variety of cotton is fairly consistent. Therefore the micronaire index will more likely indicate maturity variation than variations in fineness. Table 1 shows range of micronaire readings from different cotton cultivars.

Maturity. Cotton fiber maturity is described as the total cell wall thickness related to the diameter or width of the fiber. A mature fiber is defined as one in which twice the cellulose wall thickness equals or exceeds the width of the lumen.

Arealometer. Arealometer is an air flow instrument responsive to specific area and immaturity ratio. Hence, it has been used to measure cotton fineness and immaturity. Specific area (A) is defined as the ratio of the external surface of the fibers to the volume of fibrous material. Immaturity ratio (I) is defined as the area of a circle having the same perimeter as an average fiber to the actual cross section area of the fiber (Hertel and Craven, *Textile Research J.* 21; 265–774, 1951). Other parameters calculated or measured by Arealometer include perimeter (P), weight fineness in terms of area density of cellulose (W), and wall thickness (T). The increase in apparent specific area produced by compression in arealometer (D) is related to $I^2$.

Analysis of Transgenic Cotton Containing Antisense and Sense Genes

Fiber properties were measured by either Star Lab (2121 Dutch Valley, Knoxville, Tenn.) or by Cotton Incorporated (Raleigh, N.C.). Table 2, below, shows transgenic cotton plants containing various cDNA and genomic DNA constructs. Transgenic plants and fibers from each of these groups were analyzed. The fiber measurements for each group are presented in the following sections.

Transgenic cotton containing antisense E6 gene. We generated a number of DP-50 transgenic cotton containing antisense E6 gene. Star Lab Inc. measured the fiber properties using Stelometer readings. The results are shown in Table 3, below. There are three plants that show significantly reduced fiber strengths, #17-55-62, 17-55-67 and 17-114-01.

We analyzed the fibers of one transgenic plant that showed reduced strength (#17-55-67) and one that showed normal strength (#17-55-02) by northern and western blot techniques. Northern analysis of 17-55-67 fiber RNA showed that the E6 transcript level is reduced by 95% or more compared to control DP 50 fibers RNA. One the other hand, #17-55-02 showed less than 5% reduction in E6 transcript level.

The E6 proteins of these plants were then analyzed by western blots. Plant #17-55-67 showed a 95% reduction in E6 protein levels compared to normal DP 50 fibers while plant #17-55-02 showed no reduction in E6 levels. Thus, both northern and western blot analyses indicate that E6 gene expression in #17-55-67 is significantly reduced.

Plant #17-55-67 is an epidermal transformant. Therefore, the progeny of this plant will not carry the antisense E6 gene. If the reduction in #17-55-67 fiber strength is due to the reduction of E6 proteins, then the progeny of #17-55-67 should be normal. This was tested by examining the fibers of two progenies (#17-55-67R1A and B) and the results are shown in Table 3. Fibers of both #17-55-67R1A and 17-55-67R1B appear normal.

Transgenic Cotton Containing the H6 Gene (MS 600). We have completed extensive characterization of the H6 gene and its protein in cotton fiber. H6 gene encodes a pro-line rich cell wall protein that is unique to cotton fiber. An antibody against a synthetic peptide of H6 protein was used to immunoprecipitate in vitro-synthesized H6 protein. The antibody also reacts with cell wall-isolated proteins in Western blots and not with cytosolic proteins. More significantly, in collaboration with Texas Tech University, we localized H6 protein to fiber secondary cell wall. For this analysis, H6 antibody and protein A tagged with colloidal gold were reacted with 10 and 23-day fibers and subjected to electron microscopy analysis. Positive recognition occurred only in 23-day fibers. The antibody reaction was confined to the secondary cell wall. This is in agreement with our immunoprecipitation results where maximal amount of H6 gene product was observed in 15 to 23-day old fibers. The H6 antibody did not react with cotton ovules, root hairs or Arabidopsis leaf tissue. These results imply that H6 proteins are present in cotton fiber secondary cell wall and that they may have functions in their architecture. We therefore assume that H6 protein is an integral part of the matrix that binds and stabilizes cellulose microfibrils in cotton cell wall.

Fiber properties of DP-50 transgenic plants containing MS 600 (containing the H6 gene) were analyzed by Star Lab Inc. Table 4 shows the strength, length and micronaire of these fibers. There were three plants that showed greater strength (more than 21 gm/tex). Plant #17-16-11 (a germ line transformant) showed a 26% increase compared to control DP 50 fiber. At present the progenies of these plants are being analyzed.

Transgenic Plants Containing Kapok Gene /KPO-4). Kapok tree produces fibers that are somewhat similar to cotton fibers. However, the kapok fibers are weak compared to cotton fiber and have exceptionally fine fiber (low micronaire), as shown in Table 5, below. We investigated the effect of expression of kapok gene on cotton fiber properties by incorporating the kapok gene into cotton. The transgenic plants were then tested for fiber properties and the results are shown in Table 6, below. Of the 18 plants generated, two plants, #17-67-47 and #17-56-07, have very low micronaire readings of 2.8 and 2.4 respectively. These plants are being further studied.

Analysis of Transgenic Plants Containing Antisense B12 (AS-61). We identified one transgenic plant, #YUS-98-2#2, containing the antisense B12 gene, to be superior in strength (Table 7, below). #YUS-98-2#2 is an epidermal transformant that showed a 28% increase in fiber strength. We examined the progeny of the transformant to determine whether the increased strength was due to the germplasm or due to the transgene. When two progenies (#YUS-98-2#2R1A and YUS-98-2#2R1B) of this plant were analyzed, both of them showed normal fiber strength (Table 7). From this we conclude that the B12 gene may have a negative role in the maintenance of fiber strength.

Conclusions. We have assumed that many of the fiber-specific cDNA clones that we have isolated may have important functions in the development of cotton fiber. This was based on the logic that if a protein is preferentially expressed in a given cell type, then it is likely that the protein may have some critical role in its development. We have proven this concept in a number of instances by causing either over-expression or reduced expression of the genes and observing discernable fiber property changes.

TABLE 1

| | | Fiber Properties* of Cotton Cultivars | | | | | | | | |
|---|---|---|---|---|---|---|---|---|---|---|
| | | Strength (gm/tex) | | | Length (inches) | | | Micronaire | | |
| Variety | # Plants | Ave. St. (SD) | Max. | Min. | Ave. (SD) | Max. | Min. | Average (SD) | Max. | Min. |
| DP 50 | 35 | 18.9 (0.834) | 20.6 | 17.5 | 1.157 (0.037) | 1.24 | 1.10 | 4.005 (0.396) | 4.8 | 3.0 |
| DP 90 | 35 | 21.84 (0.892) | 23.6 | 19.9 | 1.145 (0.04) | 1.21 | 1.07 | 3.926 (0.269) | 4.6 | 3.5 |
| C 312 | 20 | 19.490 (0.527) | 20.9 | 18.7 | 1.192 (0.030) | 1.22 | 1.12 | 3.875 (0.429) | 4.7 | 3.2 |
| Pima | 30 | 26.817 (1.299) | 29.5 | 23.6 | 1.214 (0.039) | 1.31 | 1.15 | 3.553 (0.235) | 3.8 | 2.9 |
| Sea Island | 8 | 27.763 (1.80) | 30.9 | 24.3 | 1.459 (0.079) | 1.62 | 1.36 | 2.913 (0.127) | 3.0 | 2.7 |

*All are stelometer data of inner boll fibers grown under similar conditions.
SD = Standard Deviation

TABLE 2

| Plasmid | Discription | # Epidermal | # Germline | Comments |
|---|---|---|---|---|
| AS-52 | E6 promoter, antisense E6; 35S-Gus. | 7 | 0 | |
| AS-53 | E6 promoter, antisense H6; 35S-Gus | 6 | 1 | |
| AS-58 | 35S promoter, antisense E6; | 30 | 0 | |

TABLE 2-continued

| Plasmid | Discription | # Epidermal | # Germline | Comments |
|---|---|---|---|---|
| AS-61 | 35S-Gus 35S promoter, antisense B12; 35S-Gus | 4 | 1 | |
| MS 600 | E6 promoter, H6 gene; 35S-Gus | 9 | 2 | |
| KP04 | Kapok Gene; 35S-Gus | 17 | 1 | |
| AS-60 | 35S promoter, antisense B8; 35S-Gus | 4 | 1 | |
| AS-67 | 35S promoter: antisense of E6, H6, B8, B12; 35S GUS | 13 | 4 | Mixture of Plasmids were used for transformation. |
| AS-72 | E6 promoter: antisense of E6, H6, B8, B12 and 35S Gus | 3 | 3 | Mixture of Plamids were used for transformation. |

AS-67 is a mixture of four antisense genes introduced into cotton.
AS-72 is a mixture of four antisense genes introduced into cotton.

TABLE 3

Fiber Properties* of Plants Containing Antisense E6 Gene.

| Plant # | Strength gm/tex | Length (inches) | Micronaire |
|---|---|---|---|
| AS-52 | | | |
| 16-173-77 | 19.0 | 1.0 | 4.5 |
| 16-173-89 | 21.7 | 1.10 | 3.6 |
| 16-173A-06 | 19.2 | 1.07 | 3.6 |
| 17-055-62 | 17.0 | 1.05 | 4.1 |
| 17-47-25 | 17.8 | 1.08 | 4.5 |
| 17-55-62 | 18.9 | 1.11 | 4.2 |
| 17-55-32 | 17.3 | 1.15 | 4.1 |
| 17-55-02 | 16.3 | 1.07 | 3.9 |
| 17-55-67 | 16.3 | 1.08 | 3.9 |
| 17-55-67 RIA* | 18.9 | 1.19 | 4.2 |
| 17-55-67 RIB* | 18.6 | 1.16 | 3.8 |
| AS-58 | | | |
| 17-106-02 | 18.4 | 1.11 | 4.0 |
| 17-106-06 | 18.1 | 1.15 | 4.0 |
| 17-107-08 | 18.0 | 1.19 | 4.1 |
| 17-107-18 | 18.3 | 1.10 | 3.7 |
| 17-107-21 | 18.5 | 1.15 | 4.2 |
| 17-109-22 | 19.8 | 1.17 | 4.4 |
| 17-114-01 | 15.7 | 1.05 | 3.9 |
| 17-114-04 | 20.2 | 1.13 | 3.7 |
| Control DP-50 | 18.9 | 1.15 | 4.005 |

*All are stelometer data
**17-55-67 RIA and B are progenies of 17-55-67.

TABLE 4

Transgenic Fiber Analysis # MS 600

| Plant # | Strength gm/tex | Length (inches) | Micronaire |
|---|---|---|---|
| 17-16-06 | 19.5 | 1.14 | 3.9 |
| 17-15-01 | 18.6 | 1.15 | 4.6 |
| 17-15-02 | 21.3 | 1.13 | 3.4 |
| 17-16-06 | 18.8 | 1.10 | 4.0 |
| 17-16-08 | 21.6 | 1.05 | 3.2 |
| 17-16-09 | 20.4 | 1.15 | 3.9 |
| 17-16-10 | 17.4 | 1.09 | 3.7 |
| 17-16-11 | 23.9 | 1.20 | 3.7 |
| SC26-04 | 18.0 | 1.15 | 4.7 |
| Control DP-50 | 18.9 | 1.10 | 4.0 |

All are stelometer data
All are DP-50

TABLE 5

Kapok Fiber Properties: HVI Results

| Variety | Strength gm/tex | Length (inch) | Micronaire |
|---|---|---|---|
| DP-50 | 25.3 | 1.16 | 3.9 |
| Kapok | 10.0 | 0.78 | 2.0 |
| Pima | 36 | 1.38 | 3.5 |

HVI Strength measured by HVI shows diference from that measured by stelometer.

TABLE 6

Fiber Properties of Transgenic Cotton Containing KPO-4 Gene

| Plant # | Strength gm/tex | Length (inches) | Micronaire |
|---|---|---|---|
| 17-67-47 | 15.5 | 1.07 | 2.8 |
| 17-56-03 | 18.1 | 1.15 | 4.3 |
| 17-56-04 | 18.3 | 1.01 | 4.1 |
| 17-56-07 | 16.3 | 0.99 | 2.4 |
| 17-56-10 | 18.4 | 1.15 | 4.6 |
| 17-56-11 | 18.2 | 1.23 | 4.2 |
| 17-58-10 | 21.6 | 1.15 | 3.7 |
| 17-67-24 | 19.3 | 1.19 | 3.7 |
| 17-67-36 | 18.2 | 1.21 | 3.5 |
| 17-67-40 | 18.3 | 1.13 | 4.2 |
| 17-67-43 | 19.5 | 1.13 | 3.4 |
| 17-67-44 | 19.9 | 1.14 | 4.0 |
| 17-67-46 | 18.2 | 1.17 | 3.5 |
| 17-67-47 | 19.7 | 1.14 | 3.5 |
| 17-67-48 | 21.1 | 1.15 | 4.3 |
| 17-67-51 | 18.5 | 1.17 | 3.4 |
| 17-67-52 | 17.5 | 1.15 | 3.9 |
| 17-67-53 | 19.4 | 1.09 | 4.6 |
| Control DP-50 | 18.9 | 1.10 | 4.0 |

All are Stelometer Data
All are DP-50

TABLE 7

Transgenic Fiber Analysis of Anti B12 Gene

| Plant # | Strength gm/tex | Length (inches) | Micronaire |
|---|---|---|---|
| yus-98-2#2 | 24.2 | 1.13 | 3.9 |
| yus-98-2#2 RIA* | 17.9 | 1.20 | 3.8 |
| yus-98-2#2 RIB* | 18.7 | 1.15 | 3.1 |
| yus-98-2#3 | 18.0 | 1.19 | 4.2 |
| Control DP-50 | 18.9 | 1.15 | 4.0 |

All are Stelometer Data
All are DP-50

What is claimed is:

1. A method of producing transgenic cotton plants that produce fiber of altered strength comprising the steps of
   (a) constructing a plant expression vector which comprises in sense orientation either a protein coding sequence from SEQ ID NO:2 or nucleotide sequence encoding H6 protein and which will express that sense-oriented sequence when introduced onto cotton cells;
   (b) introducing the plant expression vector into a cotton plant so that the sense-oriented sequence in the plant expression vector is expressed in the fiber cells of the resulting transgenic cotton plant to produce a protein product;
   (c) selecting transgenic cotton plants of step (b) which have a fiber strength different from that of the untransformed cotton plant; and
   (d) propagating the transgenic cotton plants of step (c).

2. A method of producing transgenic cotton plants that produce fiber of altered strength comprising the steps of
   (a) constructing a plant expression vector which comprises in antisense orientation either SEQ ID NO:1 or a nucleotide sequence encoding E6 protein which will express that antisense-oriented sequence when introduced into cotton cells;

(b) introducing the plant expression vector into a cotton plant so that the antisense-oriented sequence in the plant expression vector is expressed in the fiber cells of the resulting transgenic cotton plant to produce an antisense RNA;

(c) selecting transgenic cotton plants of step (b) which have a fiber strength different from that of the untransformed cotton plant; and (d) propagating the transgenic cotton plants of step (c).

* * * * *

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 983 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 15 day old fiber cells
        ( F ) TISSUE TYPE: fiber cells ( v i i ) IMMEDIATE SOURCE:
        ( A ) LIBRARY: CKFB15A1
        ( B ) CLONE: E6

( x i ) SEQUENCE DESCRIPTION: SEQ ID NO:1:

```
ACACACACAA  GTAAAGCATT  AGCAACCATA  GCCATGGCTT  CCTCACCAAA          50
ACTCTTCTCT  ATGTCTATCC  TCTTCCTTTT  TGCCCTCTTC  TCCATGCAAA         100
TCCATGCTAG  AGAGTACTTC  AGCAAATTCC  CAAGAGTTAA  CATCAATGAG         150
AAAGAGACAA  CAACCAGAGA  GCAAAAGCAC  GAGACCTTCG  TTCCCCAGAC         200
CACCCAAAAG  CCAGAAGAAC  AAGAGCCAAG  GTTCATTCCT  GAAACCCAAA         250
ATGGTTATGG  CCTTTACGGC  CACGAGTCAG  GCTCAAGCCG  GCCCAGTTTC         300
ACCACCAAAG  AAACCTATGA  ACCCTATGTC  ACCCCTGTTA  GATTCCACCC         350
TGATGAGCCC  TATAACAGCA  TCCCCGAATC  CTCCAACAAT  AAAGACACTT         400
ACTACTACAA  CAAGAATGCC  TACGAGTCCA  CTAAGCAGCA  AAACTTGGGC         450
GAGGCCATTT  TCACCGAGAA  AGGATGGAGC  ACCAAGGAAA  ACCAGAACAA         500
CAACTACTAC  AACGGCAACA  ATGGTTACAA  CAATGGCGAG  AAGCAAGGCA         550
TGAGCGATAC  TAGGTACTTG  GAGAATGGAA  AGTACTACTA  TGACGTCAAG         600
AGTGAGAACA  ACTATTATCC  AAACCGGTTC  GACAACTCAA  GAGGAGTTGC         650
TTCGAGGAAC  GAGTTCAATG  AGAATCGTTA  CAACAACATG  GGAAGGTACC         700
ACCAGAACCA  AGAGGAGTTC  GAGGAAAGCG  AGGAAGAGTT  CGAACCCTGA         750
TCACCTGTCG  TACAGTATTT  CTACATTTGA  TGTGTGATTT  GTGAAGAACA         800
TCAAACAAAA  CAAGCACTGG  CTTTAATATG  ATGATAAGTA  TTATGGTAAT         850
TAATTAATTG  GCAAAAACAA  CAATGAAGCT  AAAATTTTAT  TTATTGAGCC         900
TTGCGGTTAA  TTTCTTGTGA  TGATCTTTTT  TTTTATTTTC  TAATTATATA         950
TAGTTTCCTT  TGCTTTGAAA  TGCTAAAGGT  TTG                            983
```

( 2 ) INFORMATION FOR SEQ ID NO:2:

( i ) SEQUENCE CHARACTERISTICS:
        ( A ) LENGTH: 913 base pairs
        ( B ) TYPE: nucleic acid (C) STRANDEDNESS: single
(D) TOPOLOGY: linear (ii) MOLECULE TYPE: cDNA to mRNA (iii) HYPOTHETICAL: no (iv) ANTI-SENSE: no (vi) ORIGINAL SOURCE:
(A) ORGANISM: Gossypium hirsutum
(B) STRAIN: Coker 312
(D) DEVELOPMENTAL STAGE: 15 day old fiber cells
(F) TISSUE TYPE: fiber cells (vii) IMMEDIATE SOURCE:
(A) LIBRARY: CKFB15A1
(B) CLONE: H6

(xi) SEQUENCE DESCRIPTION: SEQ ID NO:2:

| | | | | | |
|---|---|---|---|---|---|
| TTTCACACGG | GTTGTGGCGT | AGTTTAAGCA | GAGAGGGTGC | GCAGGATAAA | 50 |
| GCTATTCACC | ATTGTTTCAA | CATGAAGGTT | TGTAATAAAA | ATTTGTTTCT | 100 |
| ATCAGCATTG | CTTTGCATTG | CTGTTGCAGG | AGTTTTGGGT | CAAGCTCCTA | 150 |
| GTAATCCTCC | TACGTCTACG | CCGGCGACAC | CCACACCACC | GGCTTCTACT | 200 |
| CCTCCTCCGA | CGACTCAAGC | ACCGCCTACA | CCAACCGCCA | CTCCGCCACC | 250 |
| GGTTTCTACT | CCTCCTCCCA | CTTCATCACC | GCCCCAGTG | ACAGCTTCTC | 300 |
| CACCCCCAGT | TTCAACTCCT | CCACCCAGTT | CTCCTCCTCC | TGCAACTCCA | 350 |
| CCACCTGCTT | CTCCTCCTCC | TGCAACTCCA | CCTCCAGCTT | CTCCACCTCC | 400 |
| TGCCACTCCT | CCACCAGCTT | CTCCACCTCC | CGCCACTCCA | CCACCTGCAA | 450 |
| CCCCACCGCC | AGCAACTCCT | CCTCCTGCTA | CCCCACCACC | AGCTCCATTG | 500 |
| GCTTCTCCTC | CAGCCACAGT | CCCAGCTATC | TCTCCAGTAC | AAACACCATT | 550 |
| GACCTCGCCA | CCAGCTCCGC | CGACCGAGGC | CCCAGCACCT | ACCCTCGGGG | 600 |
| CTGCTACGCC | AGGTCCAGCT | GGAACAGACA | CGAGCGGAGC | AAATCAAATG | 650 |
| TGGACCGTAC | AAAAGATGAT | GGGAAGCTTA | GCCATGGGAT | GGGCTCTGCT | 700 |
| CAATCTGATG | GTTTAAAACA | ACCGTGTGCC | TCACATTTGA | TGCCATAGCT | 750 |
| GTGTAATGTT | TCATTCAATT | GCTTATTTCG | GCCTTGTTTT | TCTCGTATTT | 800 |
| TATGGGCTGA | TGTCTCATAT | GGGACTTTTC | TACTATACGT | ATATGAGAGC | 850 |
| CTACATTACT | TTACCATTAT | ATTGTATTCT | TTGAGACATT | ATTATTATTT | 900 |
| TTTTACCTTT | TGA | | | | 913 |

(2) INFORMATION FOR SEQ ID NO:3:

(i) SEQUENCE CHARACTERISTICS:
(A) LENGTH: 659 base pairs
(B) TYPE: nucleic acid
(C) STRANDEDNESS: single
(D) TOPOLOGY: linear (ii) MOLECULE TYPE: cDNA to mRNA (iii) HYPOTHETICAL: no (iv) ANTI-SENSE: no (vi) ORIGINAL SOURCE:
(A) ORGANISM: Gossypium hirsutum
(B) STRAIN: Coker 312
(D) DEVELOPMENTAL STAGE: 15 day old fiber cells
(F) TISSUE TYPE: fiber cells (vii) IMMEDIATE SOURCE:
    (A) LIBRARY: CKFB15A1
    (B) CLONE: C12

(xi) SEQUENCE DESCRIPTION: SEQ ID NO:3:

| | | | | | |
|---|---|---|---|---|---|
| CAACAATCAG | CAATACTCCA | AGCAACCATT | TTCCTTACAA | GTTTGTTTTT | 50 |
| CTTGTGATTA | ATCCATATGG | CTAGCTCAAT | GTCCCTTAAG | CTTGCATGTC | 100 |
| TGTTGGTGTT | GTGCATGGTG | GTGGGTGCAC | CCCTGGCTCA | AGGGGCCATA | 150 |
| ACCCGTGCTG | ATGGCTTAGT | CGGCCTCCCA | CGCTGCCTTC | CTTTTTTGTC | 200 |
| AGGGAATGGT | GATGGTGCTG | ATGCCACAGG | TTGCTGTGCC | ATCGTCATGA | 250 |
| ATGCCTTGGG | ATCGCTCTGT | GGTGATACAT | AGGAACCGAT | CTAGCTTGAA | 300 |
| ATCGGGTTCG | GATTTGGGTG | GAATTTCAAA | TTGGTGTGTT | ATGGAATCCC | 350 |
| AACTTAATCG | TGTTTAAGGG | TGGGATCCAA | TTGTGTGATA | CATTACAGAG | 400 |
| CATGGTTGTG | GATTGTTTTC | TCATATGTTT | TGATTGACTT | GCTTGCTACA | 450 |
| TTGGATGATT | TGATAAGGTG | ACCAGTTTAC | CTGGGTATCC | AACCATCATC | 500 |
| GGATTACTTT | TTAATAATTT | TTTGTTTCTT | GTTTATGTTG | TCTGCCTTTT | 550 |
| TGTTTCTTGA | TCTATAATAT | TATATTTGGC | CAAATTTCTC | ATTTTCCAGA | 600 |
| TGTAGCTTAT | ATATATATAT | TCAATAAAGT | ATATTGGTTT | AAAAAAAAAA | 650 |
| AAAAAAAAA | | | | | 659 |

(2) INFORMATION FOR SEQ ID NO:4:

(i) SEQUENCE CHARACTERISTICS:
        (A) LENGTH: 690 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Gossypium hirsutum
        (B) STRAIN: Coker 312
        (D) DEVELOPMENTAL STAGE: 15 day old fiber cells
        (F) TISSUE TYPE: fiber cells (vii) IMMEDIATE SOURCE:
        (A) LIBRARY: CKFB15A1
        (B) CLONE: B8

(xi) SEQUENCE DESCRIPTION: SEQ ID NO:4:

| | | | | | |
|---|---|---|---|---|---|
| CACCAACGGA | CAATGCTTTC | TCCAGCCTTA | AATCGGGCAC | ATTGAATTCA | 50 |
| CTCACCGATG | AACAAAAAGT | GGAGCTGGTG | CAATTCCACA | TCGTCCCAAC | 100 |
| ATACCTCACC | TCGTCTCAGT | TCCAAACCAT | TAGCAATCCT | TTGAGAACCC | 150 |
| AAGCTGGTGA | TAGTGGCGAT | GGCAAGTTCC | CTCTCAATAT | CACCACTTCG | 200 |
| GGGAACTCCG | TGAATATAAC | AACAGGGTTG | ACAAACACCA | GTGTTTCCGG | 250 |
| CACTATTTAC | ACTGATGGTC | AGCTTGCTGT | TTATCAAATC | GATCAAGTTC | 300 |
| TTCAACCATT | GCAAATATTT | GCACCTAGGC | CTCCAGCTCC | AGCACCGGCA | 350 |
| CCGGCAAAGT | GCAAGAATAA | GAAGGCTACC | ACCGTTGCTG | ATAGCCCCGA | 400 |
| TGTTACCCCA | GCTGATAACT | CCAAAGCGGC | CACCTTGCAA | AATGTTGGTT | 450 |
| TGTTTGGAGT | TGCTGCTCTA | GTTATTGCAC | TTTCTTTGTG | ACCATGAAAA | 500 |

| | | | | |
|---|---|---|---|---|
| TGGAGAAAAG | AAGAAGACAG | TGATTTTGAT | GGTGATCAAG | ATGGCGAGTG | 550 |
| TTTTTTATTT | TTTCAATAAT | TATCATTTAA | AAAATTTATG | TTCTGTATGA | 600 |
| ANGATTGAAT | TTTGAGTTTG | TCTTGTTGAT | TTCATTTATT | TTTGTTTTGA | 650 |
| AATTTTCTTT | GTTATCTCTT | ATTTCTCAAT | TGTAATTGTG | | 690 |

( 2 ) INFORMATION FOR SEQ ID NO:5:

( i ) SEQUENCE CHARACTERISTICS:
        ( A ) LENGTH: 727 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: B12

( x i ) SEQUENCE DESCRIPTION: SEQ ID NO:5:

| | | | | |
|---|---|---|---|---|
| ATAACCGTGA | CAGCCACCAA | CTTTTGTCCA | CCTAACTATG | CTTTATCTAG | 50 |
| TGACAATGGC | GGGTGGTGCA | ATCCCCCACG | AGAACACTTT | GATTTGGCCG | 100 |
| AACCGGCATT | CTTGCGGATA | GCAGAATATC | GAGCTGGAAT | CGTCCCTGTT | 150 |
| ATGTTCAGAA | GGGTGTCATG | TGTGAAGAAA | GGAGGCATCA | GGTACACCAT | 200 |
| GAATGGACAT | TCGTACTTCA | ACATGGTGTT | GATAACGAAC | GTGGGAGGGG | 250 |
| CAGGGGATAT | AACGTCAGTG | TCCATCAAGG | GTTCCAGAAC | AGGATGGCTA | 300 |
| CCTATGTCCA | GAAATTGGGG | CCAAAACTGG | CAGAGCAATG | CTTACCTTAA | 350 |
| CGGACAAAGC | CTCTCTTTTA | AAGTGACTGC | CAGCGATGGC | AGGACTATCA | 400 |
| CAGCCTACAA | TGTAGTGCCT | GCTGGTTGGC | AATTCGGACA | AACTTTTGAA | 450 |
| GGAGGCCAGT | TTTAAGACAA | TATTATAGTG | TCTGTCTAAT | ATAAAACTGG | 500 |
| AATTGACATA | TTACTTATAT | AAGGCACATG | AGCGTTTTAT | GCCGAGGTAG | 550 |
| CAAAATGGCG | CCCGCTGGCT | TTATGTGTGA | AATAGGCGAG | CAAGTGCCAT | 600 |
| TAGCCTATAA | TCTATACATT | TCTTATAGTG | AACCAAACTA | TTAAGTTTGA | 650 |
| ACTCTAGAGG | ATATATCCAT | AATGTCTGAA | ATTTGTTTGT | TGATGATTGA | 700 |
| CCATGATATT | TATGCTTTTC | ATTATTG | | | 727 |

( 2 ) INFORMATION FOR SEQ ID NO:6:

( i ) SEQUENCE CHARACTERISTICS:
        ( A ) LENGTH: 989 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no (v i) ORIGINAL SOURCE:
    (A) ORGANISM: Gossypium hirsutum
    (B) STRAIN: Coker 312
    (D) DEVELOPMENTAL STAGE: 10 day old fiber cells
    (F) TISSUE TYPE: fiber cells (v i i) IMMEDIATE SOURCE:
    (A) LIBRARY: CKFB10
    (B) CLONE: A11

(x i) SEQUENCE DESCRIPTION: SEQ ID NO:6:

| | | | | | |
|---|---|---|---|---|---|
| TAAAAGGATA | GCATCTGCCC | TTACAAAGAT | GAAATACAA | GCAAAATCGA | 50 |
| AGACTTCAGA | GATCATCCTT | AAAAGTTGAA | CACAAAGTTA | ACTTGAAATA | 100 |
| CCAGCTAAAG | TGATAATAAA | ACTCGACCAT | AGAATTTCGG | AAACTTCGAA | 150 |
| ACATTCACCA | AATAAAACCG | TCCCTCGAAT | TTCAACTATC | AAACAGTAAG | 200 |
| GCTCAACTCA | CAAAAGCCTT | GGAAAGAGGT | ACACAAATGT | TTTATCCTAC | 250 |
| TTATTCATTC | AATCAATAAA | ATAAATGGAA | CATGAACTCC | ATCCTCCTTG | 300 |
| GTTTGACAAT | ACCAGCTTTC | ACAATTAAGA | TTCTATACCA | GATTCATGAG | 350 |
| CTTGAACGGA | ATCACTCTGA | AACAATTACT | ACATGTAACA | ATGGAAACGA | 400 |
| AATGGAAAAA | CAAAAAAAAG | TTGGTTTAAT | TAATTATTAG | TTACCCTTGA | 450 |
| AGACCTTGGC | ATTGGTGGAG | TAACTCTTGG | CATGAAAGTC | TGAGAACAAG | 500 |
| TAGAGAAGAG | AGACGTTGAA | GGCTCCATTG | AAACACCAAC | TCAGAATCCC | 550 |
| AGAGCAGCCA | GAAGCAGTGA | AGTGGTAGAA | CACAAGCATG | GCCATGATCA | 600 |
| AAAAGCTTAA | CCGGAACTGC | ACCAGTTGAA | AATCCGTCAC | CATTTCTTC | 650 |
| CACTTGGGGT | GCATCCCCAG | GGTGCACAAC | AGGTAATAGG | AGTACATTAC | 700 |
| GACATGCACC | ACGCAGTTGG | TGATCAGCAC | CATGGGTACG | GAGGACTGAG | 750 |
| CACTGTCTAA | GCAAATATAA | CACATGATGA | CCACCATGGA | GTGATGGTAG | 800 |
| ACGTGAAGGA | AGGATAGCCT | CTTCATGGAT | CCGCTGAGGA | TGATCAAAAG | 850 |
| GGTGTCCATG | AATTCAACAA | TCTTGGAGAG | GTAGAAGATG | TATGCCCAGA | 900 |
| AAAAGAGAGG | GCCCGATGGG | GATGTACCCC | TAGGGAAGCA | AACGAGGGTG | 950 |
| TTGAAGTTAG | GCACCTGGGA | GAAGATGGAA | ACGAGGCAA | | 989 |

(2) INFORMATION FOR SEQ ID NO:7:

(i) SEQUENCE CHARACTERISTICS:
        (A) LENGTH: 498 base pairs
        (B) TYPE: nucleic acid
        (C) STRANDEDNESS: single
        (D) TOPOLOGY: linear (i i) MOLECULE TYPE: cDNA to mRNA (i i i) HYPOTHETICAL: no (i v) ANTI-SENSE: no (v i) ORIGINAL SOURCE:
        (A) ORGANISM: Gossypium hirsutum
        (B) STRAIN: Coker 312
        (D) DEVELOPMENTAL STAGE: 10 day old fiber cells
        (F) TISSUE TYPE: fiber cells (v i i) IMMEDIATE SOURCE:
        (A) LIBRARY: CKFB10
        (B) CLONE: D7

(x i) SEQUENCE DESCRIPTION: SEQ ID NO:7:

5,597,718

37                                                                 38
-continued

| TTTTTTTTTT | TTTTTTTTTT | TTTTCAACCA | CCCAAAAAAA | AATTATTATT | 50 |
| ACAAAAGGCA | AAGCAAAGCA | AACTGCATAA | TATGAATACA | AAAGAAATAG | 100 |
| GATCAATACC | CTTATATATC | TATGATATAT | AAGAAAATCA | CACCAATTAC | 150 |
| ATTACAAAAT | CAAATTTATG | TCACTAATGT | AACATGATAT | ATATAGAGAT | 200 |
| ATTTAAAACT | TTAGAGAAAT | TGAAAATTGA | TAACACCCAA | ATATTATCTC | 250 |
| GGAGAAGATT | AGAGGCTACT | CCCCTCATCA | CCAGTGAGAG | TGAAATTAAG | 300 |
| GGTAGCCAAT | GTCATAAAGT | CTTGAAAAGC | TTTGAATTCA | ATGCACCAAG | 350 |
| AGAGCAATTA | AAGAGACCAA | CATGGAAGAG | CATAAGAAGA | CAGCGGAAAC | 400 |
| CGGCAAAGCA | GAGCCTGCTC | CGGTAGCCAT | TGCAGGAGAA | GGAGCAATAT | 450 |
| CCTGTGCCAT | GGTCCCGGAC | ACAACAAACA | TGGCCACAGC | AAATATTG | 498 |

( 2 ) INFORMATION FOR SEQ ID NO:8:

( i ) SEQUENCE CHARACTERISTICS:
        ( A ) LENGTH: 668 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: C2

( x i ) SEQUENCE DESCRIPTION: SEQ ID NO:8:

| TTTTTTAAAC | AAAAGCATAG | TAGTTTTTAT | ACCCCACTGG | TGAAGAATGA | 50 |
| CAAACACAGT | TTCCAAATTC | AAATGCATCA | TCTAAACAAA | TATGCCCCTT | 100 |
| TCTTAGTCTT | ATCTGCATGG | TTTTGCTTGC | TGGAAATGAA | AAAGCAAAAA | 150 |
| TGAAAGAAAA | AGAAAAAAGG | TGAAAACAAC | CTTCAAGGTT | TAAGAGATGA | 200 |
| TATGTAATTT | TTCACTTTTT | TCAACGCATT | GCAGCAAGAG | GGTTCCTTTT | 250 |
| CCATTGCAGA | GGCTGATATG | TCTTCTCTGT | TTCCTCTATT | TTAGTCCATG | 300 |
| GTAATTTGTG | TTTAGCCACC | TTTCGCTTCC | TAGCTGATAC | TCCCAGATAG | 350 |
| TCTCCAGCGT | TCTTGAGGCA | GAGTCCTTCT | TGGACATCAC | AAATGGGGTA | 400 |
| ATCACTAGGG | CAGCAGTATT | CAGTTCCAGT | ACAGCAAACA | GCATTTTCAT | 450 |
| ATTCACAGCA | GCCGTATATT | AGGCAATAAT | CATAGAATTC | AAAAAGGCAA | 500 |
| CAGCATGTCT | CATCACTTGA | ACAATAGGAA | AAGTCTCCAC | AATCACTTGG | 550 |
| TGAAGGAGAT | GGAGGTGGTG | GTGGTGGTGG | AGTTGAAGGA | GGTGGCGGTG | 600 |
| GAGGAACACT | TGGCGATGGA | TAAGGGGATG | GTGAAGAGGA | TTGTTTAGTT | 650 |
| GGATAAGAAG | CCATGGCA | | | | 668 |

( 2 ) INFORMATION FOR SEQ ID NO:9:

( i ) SEQUENCE CHARACTERISTICS:
        ( A ) LENGTH: 609 base pairs ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: C12

( x i ) SEQUENCE DESCRIPTION: SEQ ID NO:9:

| | | | | | |
|---|---|---|---|---|---|
| TTTTTTTTTT | TTTTTTTTTT | TTTTTTTTTT | TTTTTTTTTT | TTTTTTTTTT | 50 |
| TTTTTTTTTA | TACCTGTTGA | GCATTCACAA | GTTCCCTTAA | CAATTTACTT | 100 |
| TCAAATACAC | CCAACAAAAA | TATCAAGTTT | CAACCCAAAC | ACAAATAAAA | 150 |
| CATAAAACAG | CATAACATAC | AGTAAACCAT | TTCAAGTCTT | TAACAAGCTT | 200 |
| CAAAGAATAG | AAGCTTGCAT | AACACGGAAG | CAACAGGTAA | TAAAAGACAT | 250 |
| CGTAAGCACA | CTCAATCACA | CGTACTTCTT | AGTACTCATC | ATCTTCACCC | 300 |
| TCATCACCCT | CAGCTGACTC | AGCACCAACT | TCTTCATAAT | CCTTCTCCAA | 350 |
| TGCAGCAAGA | TCCTCACGAG | CCTCTGAGAA | TTCTCCTTCT | TCCATACCCT | 400 |
| CACCAACATA | CCAGTGAACG | AAGGCACGTT | TGGCGTACAT | AAGATCAAAC | 450 |
| TTATGGTCAA | TGCGAGAGAA | GACTTCAGCA | ACACTGGTGG | AGTTAGAAAT | 500 |
| CATGCAAACA | GCTCTCTGGA | CCTTGGCGAG | ATCACCACCA | GGGACAACAG | 550 |
| TGGGTGGTTG | GTAGTTGATA | CCCCCCCCCC | CCCCTGCAGG | CATCGTGGTG | 600 |
| TCACGCTCG | | | | | 609 |

( 2 ) INFORMATION FOR SEQ ID NO:10:

( i ) SEQUENCE CHARACTERISTICS:
        ( A ) LENGTH: 432 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: C1

( x i ) SEQUENCE DESCRIPTION: SEQ ID NO:10:

| | | | | | |
|---|---|---|---|---|---|
| TTTCATTTCA | CTATATACAC | ACACACATAC | ACAAACCAAG | CAACCATGGA | 50 |
| TACAAGAAGC | AAAACACCTA | ATGAACCATA | GCTGCTTTAT | TCTAATAGTA | 100 |
| AAAACCCAAA | TACATCATAT | ATTATTTAGA | TCAGCTTCCA | TAATATGCTT | 150 |

```
AGCTTTTTTT  TCTCATTTAC  AATTGCAAGG  GTTGCAAGTG  CAGTTATCTC              200

CACATTTGCA  GCCATTTTCA  GCCCCAGTTT  CCATTTCAGC  TCCATCAAAG              250

TGCACTTTCC  GGGGTGCCAC  GCCAAGAACA  AGTGTCCCGG  TTGTGGTTTG              300

CTCAGCAAAG  TTCATCTCAG  GGTACATCTT  GCAACCGCCG  CAGCCGCTGC              350

CGCACTTGCA  ACCGGAGCCG  CAACCGCAGT  TTCCACCACA  GCAAGACATT              400

TTTCTTCACC  TCACTGATCA  CTAAAGGGCG  AT                                  432
```

( 2 ) INFORMATION FOR SEQ ID NO:11:

( i ) SEQUENCE CHARACTERISTICS:
        ( A ) LENGTH: 320 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: A8

( x i ) SEQUENCE DESCRIPTION: SEQ ID NO:11:

```
CAATCAAATT  AACTTAAAAG  AAGTGATATT  CAGGATACAA  GGCCAATGCC              50

AAACAGATTC  AACACAAACA  TAAGCTGCAT  ACATATAGGC  AACTTGAAGT              100

TATTGAATAG  ACGGGATTCA  GAGAACAAAG  CTGGTTAAAA  CATGAGGTAC              150

GATACAGATA  TTACATTGGC  ATGTTCTTCA  GAAGATTTTT  TTGGATGGCT              200

AAGTGGAACC  ACCAATTTTG  GGATGATCTG  GAGGTGAGGG  TTTTGGGATG              250

TAGGGAATAA  GAGGAGTACC  ATGCTCAATA  GGACCAGGTT  TTATGGATGC              300

TTTGGAGCTT  GGAACTGGAT                                                  320
```

( 2 ) INFORMATION FOR SEQ ID NO:12:

( i ) SEQUENCE CHARACTERISTICS:
        ( A ) LENGTH: 399 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: A9

( x i ) SEQUENCE DESCRIPTION: SEQ ID NO:12:

```
TTTTTTTTTT TTTTTTTTTT TTTTTTTTTT TTTTTTTTTT TTTTTTTTTT                   50

AAAATGGGAA ATGGAGACGA GTGATATTAA TTTGTAGATA AAGTTAATAT                  100

TACGTAGTCG CATAAAGCGG CATAGTACAC AACCCACAAC TCTGGAATTT                  150

TAACATCCAT ATTTATTCTG TAGCTATCGT TATTTTGGCT TCCACTAGCT                  200

GGTGAACTTT CCATGCCAAA ACTTCACTTG ACGCTGTTGC AGTCAGTGCT                  250

AGGGCTGATC TTGTAAGGGA TGTTGACACC GCACTTGCCT GGGAGTCCGC                  300

TTGCAATACC ATAGTTGATG CCAGAAATGC CGGCGGCCGC ACTTTTGATG                  350

CATTTGCAAG CTGCTTGCCG GTCTGGTGTT GTTGGGCGG CGGAGTTGA                    399
```

( 2 ) INFORMATION FOR SEQ ID NO:13:

( i ) SEQUENCE CHARACTERISTICS:
        ( A ) LENGTH: 1672 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: no ( i v ) ANTI-SENSE: no ( v i ) ORIGINAL SOURCE:
        ( A ) ORGANISM: Gossypium barbadense
        ( B ) STRAIN: Sea Island
        ( F ) TISSUE TYPE: fiber cells ( v i i ) IMMEDIATE SOURCE:
        ( A ) LIBRARY: EMBL-SI
        ( B ) CLONE: pSKSIE6-2AH3

( x i ) SEQUENCE DESCRIPTION: SEQ ID NO:13:

```
TCATCTTAGA TTTGCTTCAT CGTAATCACA TGAACCAAAT CAGCTATGTC                   50

TTCGATTTTT TCCTTGTAAA CACAAGGATG CCAAACCATC TTGGATCTGC                  100

TTCAGCGAAA TCATCTGAAG GTGAGATCTG CTATGTGTCT GCTCTCCATC                  150

AAAGTGAAGA TGCCAAACTT CGATTCGTTC TCTAACGATA CAGAGACGAC                  200

AAATCATCTT AGATTTGCTT CATCGTAATC ACGTGAAAGC CAAATCAGCT                  250

ATATCTTCGA TTTGCTCCTT GTAAACACAA GGATGCCAAA CCATCTTGGA                  300

TCTGCTTCAG CGAAATCATC TGAAGGTGAG ATCAGGGTTC GAACTCTTCC                  350

TCGCTTTCCT CGAACTCCTC TTGGTTCTGG TGGTACCTTC CCATGTTGTT                  400

GTAACGATTC TCATTGAACT CGTTCCTCGA AGCAACTCCT CTTGAGTTGT                  450

CGAACCGGTT TGGATAATAG TTGTTCTCAC TCTTGACGTC ATAGTAGTAC                  500

TTTCCATTCT CCAAGTACCT AGTATCGCTC ATGCCTTGCT TCTCGCCATT                  550

GTTGTAACCA TTGTTGCCGT TGTAGTAGTT GTTGTTCTGG TTTTCCTTGG                  600

TGCTCCATCC TTTCTCGGTG AAAATGGCCT CGCCCAAGTT TGCTGCTTA                   650

GTGGACTCGT AGGCATTCTT GTTGTAGTAG TAAGTGTCTT TATTGTTGGA                  700

GGATTCGGGG ATGCTGTTAT AGGGCTCATC AGGGTGGAAT CTAACAGGGG                  750

TGACATAGGG TTCATAGGTT TCTTTGGTGG TGAAACTGGG CCGGCTTGAG                  800

CCTGAGCCTG AGCCTGAGCC TGAGCCTGAC TCGTGGCCGT AAAGGCCATA                  850

ACCATTTGG GTTCAGGAA TGAACCTTGG CTCTTGTTCT TCTGGCTTTT                    900

GGGTGGTCTG GGGAACGAAG GTCTCGTGCT TTGCTCTCT GGTTGTTGTC                   950
```

| | | | | |
|---|---|---|---|---|
| TCTTTCTCAT | TGATGTTAAC | TCTTGGGAAT | TTGCTGAAGT | ACTCTCTAGC | 1000 |
| ATGGATTTGC | ATGGAGAAGA | GGGCAAAAAG | GAAGAGGATA | GACATAGAGA | 1050 |
| AGAGTTTTGG | TGAGGAAGCC | ATGGCTATGG | TTGCTAATGC | TTTACTTGTG | 1100 |
| TGTGTGATGT | GAAATTGCGA | TGATACAAAA | TCTATATATA | TGAAGCAAGA | 1150 |
| AAGGGCGATC | TTCTAGTTTT | CTATGTTGTA | AAAGATTTC | AACTCAATTA | 1200 |
| GGAGCAAGTG | GTGAATGGTG | ATGATTGTGG | TCCCTTCACA | TTACACCAAT | 1250 |
| AACAACTTTA | TCAAAGACG | CTTTCTTTTA | TGTTTGGTAT | TAATGATATA | 1300 |
| TATTTCATTT | TTCCTTGTAA | TGATCCCATT | CTCCCACACT | GCTAAACAGT | 1350 |
| TCTACAAATA | TGATATTTTT | TCCGCTATTT | CCTTAACATA | TAAAATTTTA | 1400 |
| TGTTTAGTTT | TGTACTATAT | ATCTTTACTA | ATATTAATTT | TTAATAAATT | 1450 |
| TGGTATTATC | GATCAATCAA | CCATAAACTA | AATTAGATAC | TTTTATAAGG | 1500 |
| TTATCAATTT | ATATAGAATA | ATAGTACAAA | TATACACATG | ATAGATTTTG | 1550 |
| AACCTACATA | TTTATAATTT | GTAATAATTA | TATCTTACTA | TTCAACCAAA | 1600 |
| ACCTCATTTA | GTATTTTTAT | CAATTTTTCA | AAATATATTT | GTTAAATAAT | 1650 |
| TTTACTTCAC | CCACATCGTG | AG | | | 1672 |

( 2 ) INFORMATION FOR SEQ ID NO:14:

( i ) SEQUENCE CHARACTERISTICS:
        ( A ) LENGTH: 1618 base pairs
        ( B ) TYPE: nucleic acid
        ( C ) STRANDEDNESS: double
        ( D ) TOPOLOGY: linear ( i i ) MOLECULE TYPE: Genomic DNA ( i i i ) HYPOTHETICAL: no ( i v ) ANTI-SENSE: no ( v i ) ORIGINAL SOURCE:
        ( A ) ORGANISM: Cebia pentandra
        ( B ) STRAIN: Kapok
        ( F ) TISSUE TYPE: fiber cells ( v i i ) IMMEDIATE SOURCE:
        ( A ) LIBRARY: EMBL-CP
        ( B ) CLONE: pSKCPE6-RV ( x i ) SEQUENCE DESCRIPTION: SEQ ID NO:14:

| | | | | |
|---|---|---|---|---|
| TGGTATTTAG | TATATTTAAA | TTTTAAATAT | TAATATATGT | AAAATTAAAA | 50 |
| AAAAAAATTA | GATTAGGATT | TATTTTATAA | AAAAAATGGA | AATGAGATCA | 100 |
| TAAAAGAGC | ACCAAATAAT | AATAATAAAA | GAAGAAATCA | AAGTCAATCA | 150 |
| TTAACAACAA | ACACAAAGTG | AAGAGGCCAC | TTTTGATAAA | GTCTTATGTC | 200 |
| TCGTGCAAGG | GACCACACAC | ACAATCATCA | GTTTTCACAG | TCTCCCCCCC | 250 |
| GTCCCGTTTG | CAACTAATTG | AGTAGAAAAT | TTTACAAATT | GAGGGGAAAC | 300 |
| GAAAAAATTT | GCCTTTCTAT | ATAAACATTT | CCTATCATCA | CAATTTCTCA | 350 |
| TTAGTGTGCA | CTCTCCCACG | CAAAAAAAA | AAAAAAAGA | AAGAAAGCAT | 400 |
| TAGCTAGCCT | TCCCCTTGCC | CATGGCTTCC | TCACCGAAAC | TCGTTGCTAT | 450 |
| CTTCTTCCTC | TTTGCCCTCT | GCTCCATGCA | GATTGATGCT | AGAGAATTCT | 500 |
| TCAGCAAAGT | CCCAAGTGTC | AACACCAATG | AGAAGGAGTC | AACAACCATT | 550 |
| CCTGAGACCT | TCATTCCCGT | GACGACCACC | CAAAAGACTT | TGCTTCCCAA | 600 |

| | | | | | |
|---|---|---|---|---|---|
| CAAAGAAGAG | CAGAGCACTT | TCGGGAAGAA | CGAGCAAGAG | CCAAGGTTTA | 650 |
| TCCCTGAGAC | TCAAAACGGA | TATGGCCTTT | ATGGTCACGA | GTCAGGCCAG | 700 |
| CTCCCTCCCA | GCACCACCAC | CAATACCAAA | GAAACCTATG | AACCCTATGT | 750 |
| TACCCCTGTT | AGATTCCACC | CTGATGAACC | TTACAACAGC | ATTCCTGCAT | 800 |
| CCAAAACTAA | CAACAAAAAT | ACTTACTATT | ACAACAAGAA | CCGCTATGAG | 850 |
| AATACCGAGA | AACAAAATCT | GGCTGAAGCC | AGCTTCACAG | AGAAAGGATG | 900 |
| GAGCACCAAG | GAAAACCAGA | ACAACAACAA | CTACTACAAC | GGCAACAATG | 950 |
| GGTACAACAA | GAATGCCTAT | GGAATACCG | AGCAGCAAAA | TTTGGGTGAG | 1000 |
| ACCATTTTCA | CAGAAAAGG | ATGGAGCACC | AAGGAAAACC | AGAACAACAA | 1050 |
| CTACTATAAT | GGCAACAATG | GATACAACAA | TGGTGAGAAG | CAAGGCATGA | 1100 |
| GCGACACTAG | ATTCTTGGAG | AATGGAAAGT | ACTACTATGA | TCTTAAGAAT | 1150 |
| GAGAACAACT | ACTATCCAAA | CCAGTTTGAG | AACTCCAGGG | GAGTTGCTTC | 1200 |
| AAGGAACGAG | TTCAATGAGA | ATCGTTACAG | CAACGTGGGA | AGGTACAACC | 1250 |
| AGAACCAAGA | GGAGTTCGAA | GAGAACGAGG | AAGAGTTCGA | GCCATGAGCT | 1300 |
| AGCTGTCTTG | TACTCTCTAC | AATGGAGTGA | AAAACATCAA | GCAAACAAG | 1350 |
| AAGTGGTTTT | AATTAGACGA | TAAGTATGCT | ATAATTAATT | AGCAAAAACA | 1400 |
| GTAAAGAGAA | AGATTTTATT | TATTGGGTCT | TGCGTTTAGT | TTGTGATCTT | 1450 |
| TTCATTTTCT | GGTTTGCATA | GTATCCTTTG | CTTTGCAATG | CTCAAGATAT | 1500 |
| GAGAGTCATG | CTTTTTATTT | CTTTCTACT | TTATCAAACA | ATTTATTGAA | 1550 |
| TAACAATGTA | AGTATCTCCT | AATAATCAGT | CTTCAGTTTT | CATATTCGCC | 1600 |
| TCTCTAGCAA | ATGCACCA | | | | 1618 |

( 2 ) INFORMATION FOR SEQ ID NO:15:

( i ) SEQUENCE CHARACTERISTICS:
        ( A ) LENGTH: 455 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: D4

( x i ) SEQUENCE DESCRIPTION: SEQ ID NO:15:

| | | | | | |
|---|---|---|---|---|---|
| AGCAGCTGTG | CCTAGTCCTT | CTACTATGCC | TAGAGCTTGG | ACTTTCTTCC | 50 |
| TACTCGATCA | GATTCTAACA | TACGTAATCT | GGGAGCTGC | TGCTGTTTCA | 100 |
| ACCGAGGTGC | TTTACTTAGC | AAACAAGGA | GACTCAGCCA | TCACTTGGAG | 150 |
| TGCAGCTTGT | GGGACATTTG | CTGGTTTCTG | TCATAAAGCC | ACAATAGCCG | 200 |
| TGGTGATCAC | GTTTGTTGCA | GTCATTTGTT | ATGCGGTGCT | ATCACTGGTC | 250 |

-continued

| TCTTCTTATA | GACTTTTCAC | CAAGTTTGAT | GCCCCAGTGA | ACTACCCCAG | 300 |
| TAAGACCATA | GAAGCTACTG | TTTTCCATGG | TTGATTTATG | TTATTACTGA | 350 |
| AATTAATTTA | CCTTATATTT | TCATGTTCTG | CTTGTAATAA | TAATAAAAAA | 400 |
| GGTTGCTTAC | AGTGTGTTTA | TGTTATATGA | TTAAATAGAG | GTGTTGTCTT | 450 |
| TGGTG | | | | | 455 |

( 2 ) INFORMATION FOR SEQ ID NO:16:

( i ) SEQUENCE CHARACTERISTICS:
        ( A ) LENGTH: 1080 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: B6

( x i ) SEQUENCE DESCRIPTION: SEQ ID NO:16:

| ACTACTCAAC | TTTCTCTCTG | AATTCCTCCA | AGTTAGGAGT | TTGGAGAGTG | 50 |
| GTCACCGCTG | AAGCAAAACA | AATTTCTTGG | GGGAAAAGAA | AATGGAGTTT | 100 |
| TCCATGATTT | TTATGATTAG | CTTCTCTGTA | TTGATTTTGT | GCTCCTCACT | 150 |
| GGCATATGGT | CAAGTTGCAA | TGAGCACAAA | CCCGACACCG | TCACCCTCAC | 200 |
| CAGCACCGGC | ACCGACACCG | GCATACACAA | ATATCAAAGA | CTTACTCTCT | 250 |
| GTGGCAGGTC | CATATCACAA | GTTCCTGGGC | TACCTCGAGT | CGACTAAATT | 300 |
| AATCGACACG | TTCCAAATCC | AAGCCAACAA | CACGGTTGAA | GGCATTACGA | 350 |
| TTTTCGTACC | GAAAGACAGC | GCATTCAAGG | CTCTTACGAA | GCCTTCATTG | 400 |
| TCAAATCTAA | CTGATGATCA | GTTCAAATCA | GTGCTCCTTT | ACCATGCCTT | 450 |
| GCCACGATAC | TATGCCCTTG | CGGACTTCAA | TGACCTAAGT | GAGAAAGGCC | 500 |
| CTATTAGTAC | ACTTGCTGGT | GGCCAATACA | CTTTGCAATT | CAACGATGAG | 550 |
| TCTGGTACCG | TCCGCCTCGA | TTCCGGATGG | AGCAAAACAA | AAGTCACTAG | 600 |
| CGCAGTACAT | ACGTCCAAGC | CAGTCGCAGT | CTATCAAATC | GATAAGGTCC | 650 |
| TTCTTCCGGA | GGCCATTTTC | GGGACCGACA | TACCTCCGAC | ACCTGCACCT | 700 |
| GCCCCGGCTC | TTGGTATTGG | CCCATCAGCT | GACACTCCAT | CAGCAGCAAA | 750 |
| ATCCGAAGAA | ACTGGTTCCT | CATCAAAGCC | TTCGTTTTCG | GGTTCATCAT | 800 |
| CTCCTAGGAT | CATGATGAAC | TCGGGCATTT | GGACTCAGCT | GGTTTTGGCA | 850 |
| TTCTTAGGTG | GATGGCTGGT | TCTCTTTTTC | TGAGACGTTA | TAATTTTATG | 900 |
| TTGAAAGGGG | GGCACATATG | GGGTTCTCAA | TTTTCTGTGA | TTTTTAGACC | 950 |
| CCATTTTCTT | TCATATATAT | GTTACTGTGT | GTTATTATAA | AAAGAATGTT | 1000 |
| ATTGTGTGTT | AAGAATATGG | TTGTGTTATA | ATTACCATTT | CAATTTTAAT | 1050 |
| GGAGTTTTGC | CTTAAAAAAA | AAAAAAAAA | | | 1080 |

( 2 ) INFORMATION FOR SEQ ID NO:17:

( i ) SEQUENCE CHARACTERISTICS:
        ( A ) LENGTH: 868 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:
        ( A ) ORGANISM: Gossypium hirsutum
        ( B ) STRAIN: Coker 312
        ( D ) DEVELOPMENTAL STAGE: 10 day old fiber cells
        ( F ) TISSUE TYPE: fiber cells ( v i i ) IMMEDIATE SOURCE:
        ( A ) LIBRARY: CKFB10
        ( B ) CLONE: A12

( x i ) SEQUENCE DESCRIPTION: SEQ ID NO:17:

```
CAACGATACT  TCAAATACTA  ATACATTTAT  CACCAAACCA  TTGTGATACA         50
GAAAGTAATA  TCATTTTATC  CATTACCAAG  AACATGATTC  ATGGATAGAT        100
TTCACATAAC  TAAACTCGTG  GGTATATTAT  TATAGAACAA  ACTGGATATT        150
GCTTTAAGCT  GTTTTAATGC  ACACTATGAT  GAAACTTATA  GTGTATGAAT        200
CTACTCTTCA  GGATTTTTAC  TTAGGGACCC  AAACAATGTG  ATCCCGAGGA        250
AGGAAATGGC  AGACAGGAAT  GGTTCCTGGT  TCAACTTTTA  GGACTTGAAA        300
AGCCAAATGC  TTAGGGTTCC  ATGCTGATGT  ATCTGTGTGG  CAGACTGCTA        350
CTGCTTTGGC  TTTTGTTCCG  TCAGCACCCT  CTAAAGGAAC  CATGTAAGCC        400
CTTGTTGTTT  CTGATTTATG  GCAATAGAAG  ACAGCATATG  CATAATTCTG        450
CTTGTGGCAC  ACTACGGCTT  TGTCATCTGT  CATCTTCTGC  ACTCCAGCTG        500
CTATTGTATA  CTTTTGCATT  GGGGTTTGTT  TTTCCACTTC  TGTTGAGACT        550
GCCTGATCAA  CTTTCCCTAG  TTTGGAAATG  CTATAGTCAA  TCATTGACTC        600
CAGTGAGGTT  GCACAATATT  TTTCCTCTCC  TTCAATCGCT  GGCTGTTCGC        650
ACTCCTTAAT  TGTGTTCTTC  ATCATCTCTG  CCTTCAGTGA  TCCAGGTTTC        700
ACTGAAAACT  TGTTGAAAAT  TTCTGGCAAC  TTGTCAGATG  AAAACGGTAT        750
TTTTTGGGCA  GTTTGATAAG  GTAAGAAAGC  TGATTTCTCT  GTATTTTCAG        800
TGAAATGCAG  GCTCATTGTT  GCCCCGGGGT  GCATATCCTT  TTCCAGAAAG        850
AAAAGAGCCA  CATTCGGG                                             868
```

( 2 ) INFORMATION FOR SEQ ID NO:18:

( i ) SEQUENCE CHARACTERISTICS:
        ( A ) LENGTH: 1283 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: no ( i v ) ANTI-SENSE: no ( v i ) ORIGINAL SOURCE:

(A) ORGANISM: Gossypium hirsutum
(B) STRAIN: Coker 312
(D) DEVELOPMENTAL STAGE: 15 day old fiber cells
(F) TISSUE TYPE: fiber cells (vii) IMMEDIATE SOURCE:
(A) LIBRARY: CKFB15
(B) CLONE: E9

(xi) SEQUENCE DESCRIPTION: SEQ ID NO:18:

```
ACACACAAAT ACACTAAAAA TTCTTTGCTT TCTATTTTGT AAACCATGGC        50
TCATAACTTT TGTCATCCTT TCTTCCTTTT CCAACTTTTA CTCATTACTG       100
TCTCACTAAT AATCGGTAGT CACACCGTCT CGTCAGCGGC TCGACATTTA       150
TTCCAGACAC AAACAACCTC ATCAGAGCTG CCACAATTGG CTTCAAAATA       200
CGAAAAGCAC AAAGAGTCTG AATACAAACA ACCAAAATAT CACGAAAAGT       250
ACCCAAAACA TGAGAAGCCT AAAATGCACA AGGAGGAAAA ACAAAAACCC       300
TGCAAACATC ATGAAGAGTA CCACGAGTCA CGCGAATCGA AGGAGCACGA       350
AGAGTACGAT AAAGAAAAAC CCGATTTCCC CAAATGGGAA AAGCCTAAAG       400
AGCACAAGAA ACACGAAGTT GAATATCCGA AAATACCCGA GTACAAGGAC       450
AAACAAGATG AGGATAAGGA ACATAAAAAT GAAGAGTACC ATGAATCACG       500
CGAATCGAAG GAGCACGAAG AATACGAGAA AGAAAAACCC GAGTTCCCCA       550
AATGGGAAAA GCCTAAAGAG CACGAGAAAC ACGAAGTCGA ATATCCGAAA       600
ATACCCGAGT ACAAGGAAAA GCAAGATAAG AGTAAGGAAC ATAAAGATGA       650
AGAGTGCCAC GAGTCACACG AATCGAAAGA TCACGAAGAG TACGAGAAAG       700
AAAAACCCAA TTTCTTCAAA TGGGAAAAGC CTAAAGAGCA CGAGAAACAT       750
AAAGCCGAAT ATCCAAAAAT ACCCGAGTGC AAGGAAAAAC AAGATGAGGA       800
TAAGGAAGAT AAACATGAGT TCCCAAAGCA TGAAAAAGAA GAGGAGAAGA       850
AACCTGAGAA AGGCAGAGTA CCCTGAGTGG GTTAAAATGC CTGAATGGCC       900
GAAGTCCATG TTTACTCAGT CTGGCTCGAG CATTAAGCCT TAAGCCATAT       950
GACACTGGTG CATGTGCCAT CATCATGCAG TAATTTCATG GGATATCGTA      1000
ATTATATTGT TAATAAAAAA GATGGTGAGT GGGAAATGTG TGTGTGCATT      1050
CATCCATGTA GCAATGCTGA ATCTCTTTGC ATGCATAGAG ATTCTGAATG      1100
GTTATAGTTT ATGTTATATC GTTTGTTCTA GTGAAATTAA TTTTGAATGT      1150
TGTATCTAAT GTTAACATCA CTTGGCTTGA TTTATGTTTT AATGAAGTTT      1200
ATGTTGTGTA TTTTACTTTA ATGATATTCC ATGTATTGTT AATTTAAAAA      1250
AAAAAAAAAA AAAAAAAAAA GGCCGAATTG GCA                        1283
```